(12) United States Patent
Anderson

(10) Patent No.: US 7,249,687 B2
(45) Date of Patent: Jul. 31, 2007

(54) MEDICAMENT DISPENSER

(75) Inventor: Gregor John McLennan Anderson, Ware (GB)

(73) Assignee: Glaxo Group Limited, Greenford (GB)

( * ) Notice: Subject to any disclaimer, the term of this patent is extended or adjusted under 35 U.S.C. 154(b) by 52 days.

(21) Appl. No.: 10/517,793

(22) PCT Filed: Jul. 17, 2003

(86) PCT No.: PCT/EP03/07937

§ 371 (c)(1),
(2), (4) Date: Dec. 13, 2004

(87) PCT Pub. No.: WO2004/009470

PCT Pub. Date: Jan. 29, 2004

(65) Prior Publication Data

US 2005/0258182 A1    Nov. 24, 2005

(30) Foreign Application Priority Data

Jul. 19, 2002    (GB) ................................. 0216831.8

(51) Int. Cl.
G07F 11/00 (2006.01)
A61M 15/00 (2006.01)
A61M 16/00 (2006.01)
B05D 7/14 (2006.01)
B65D 83/06 (2006.01)

(52) U.S. Cl. .......................... 221/5; 221/3; 128/203.15

(58) Field of Classification Search ................ 221/74, 221/7, 25, 26, 71, 69, 73, 82, 84, 4, 87, 13, 221/5, 8, 2; 206/531, 532; 128/203.15, 128/203.21; 700/236
See application file for complete search history.

(56) References Cited

U.S. PATENT DOCUMENTS

| | | | | |
|---|---|---|---|---|
| 3,604,559 A | * | 9/1971 | McCall et al. | 206/533 |
| 3,651,927 A | * | 3/1972 | Richardson et al. | 221/5 |
| 3,730,388 A | * | 5/1973 | Bender | 221/68 |
| 4,015,717 A | * | 4/1977 | Richardson et al. | 206/534 |
| 4,572,403 A | * | 2/1986 | Benaroya | 221/3 |
| 4,667,845 A | * | 5/1987 | Frazier et al. | 221/5 |
| 4,736,849 A | * | 4/1988 | Leonard et al. | 206/534 |
| 4,905,866 A | * | 3/1990 | Bartell et al. | 221/5 |

(Continued)

FOREIGN PATENT DOCUMENTS

EP    0884670    12/1998

(Continued)

Primary Examiner—Gene O. Crawford
Assistant Examiner—Rakesh Kumar
(74) Attorney, Agent, or Firm—Robert J. Smith

(57) ABSTRACT

A medicament dispenser for use with a medicament carrier having multiple distinct medicament doses carried thereby and an internal mechanism for dispensing the distinct medicament doses carried by the medicament carrier. The mechanism comprises receiving means for receiving the medicament carrier; release means for releasing a distinct medicament dose from the medicament carrier on receipt thereof by the receiving means; an outlet, positioned to be in communication with the medicament dose releasable by the release means; indexing means for individually indexing the distinct medicament doses of the medicament carrier; and counting means for counting each time a distinct medicament dose of the medicament carrier is indexed by the indexing means. The counting means is a distinct electronic counter unit that is reversibly receivable by the medicament dispenser.

5 Claims, 11 Drawing Sheets

U.S. PATENT DOCUMENTS

| | | | |
|---|---|---|---|
| 5,020,527 A * | 6/1991 | Dessertine | 128/200.23 |
| 5,338,157 A | 8/1994 | Blomquist | |
| 5,363,842 A | 11/1994 | Mishelevich et al. | |
| 5,409,132 A * | 4/1995 | Kooijmans et al. | 221/86 |
| 5,544,647 A | 8/1996 | Jewett et al. | |
| 5,544,661 A | 8/1996 | Davies et al. | |
| 5,575,392 A * | 11/1996 | Cutler | 206/534 |
| 5,619,984 A * | 4/1997 | Hodson et al. | 128/203.15 |
| 5,646,390 A * | 7/1997 | Wang et al. | 235/454 |
| 5,809,997 A | 9/1998 | Wolf | |
| 5,822,715 A | 10/1998 | Worthington et al. | |
| 5,860,419 A * | 1/1999 | Davies et al. | 128/203.15 |
| 5,924,074 A | 7/1999 | Evans | |
| 5,990,782 A * | 11/1999 | Lee | 340/309.7 |
| 5,992,740 A * | 11/1999 | Zocca | 235/436 |
| 6,029,659 A * | 2/2000 | O'Connor | 128/203.12 |
| 6,062,420 A * | 5/2000 | Krouwel et al. | 221/5 |
| 6,119,684 A | 9/2000 | Nohl et al. | |
| 6,142,149 A | 11/2000 | Steen | |
| 6,145,697 A * | 11/2000 | Gudish | 221/3 |
| 6,176,391 B1 * | 1/2001 | Rehkemper et al. | 221/8 |
| 6,202,642 B1 | 3/2001 | McKinnon et al. | |
| 6,234,343 B1 * | 5/2001 | Papp | 221/7 |
| 6,360,739 B1 | 3/2002 | Rand et al. | |
| 6,435,175 B1 | 8/2002 | Stenzler | |
| 6,880,722 B2 * | 4/2005 | Anderson et al. | 221/71 |
| 7,004,164 B2 * | 2/2006 | Scarrott | 128/205.23 |
| 2002/0066451 A1 | 6/2002 | Davies et al. | |

FOREIGN PATENT DOCUMENTS

| | | |
|---|---|---|
| GB | 2372543 | 8/2002 |
| WO | WO 86/02275 | 4/1986 |
| WO | WO 99/10829 | 3/1999 |
| WO | WO 99/41682 | 8/1999 |
| WO | WO 01/17597 | 3/2001 |
| WO | WO 01/24690 | 4/2001 |
| WO | WO 01/26020 | 4/2001 |
| WO | WO 01/26021 | 4/2001 |
| WO | WO 01/41846 | 6/2001 |

* cited by examiner

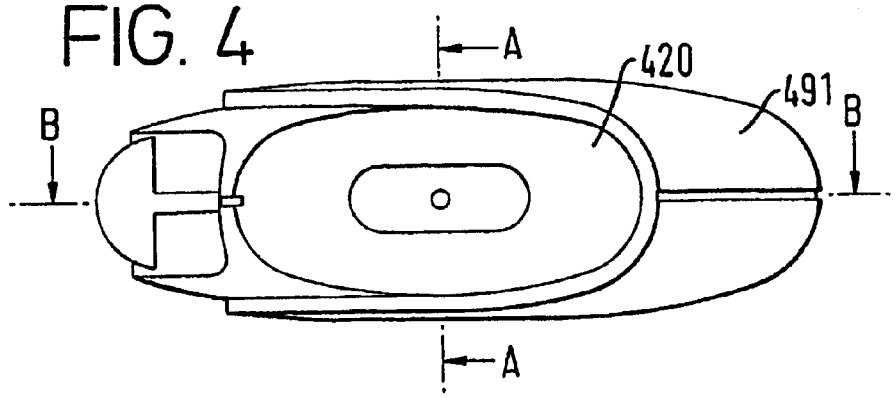
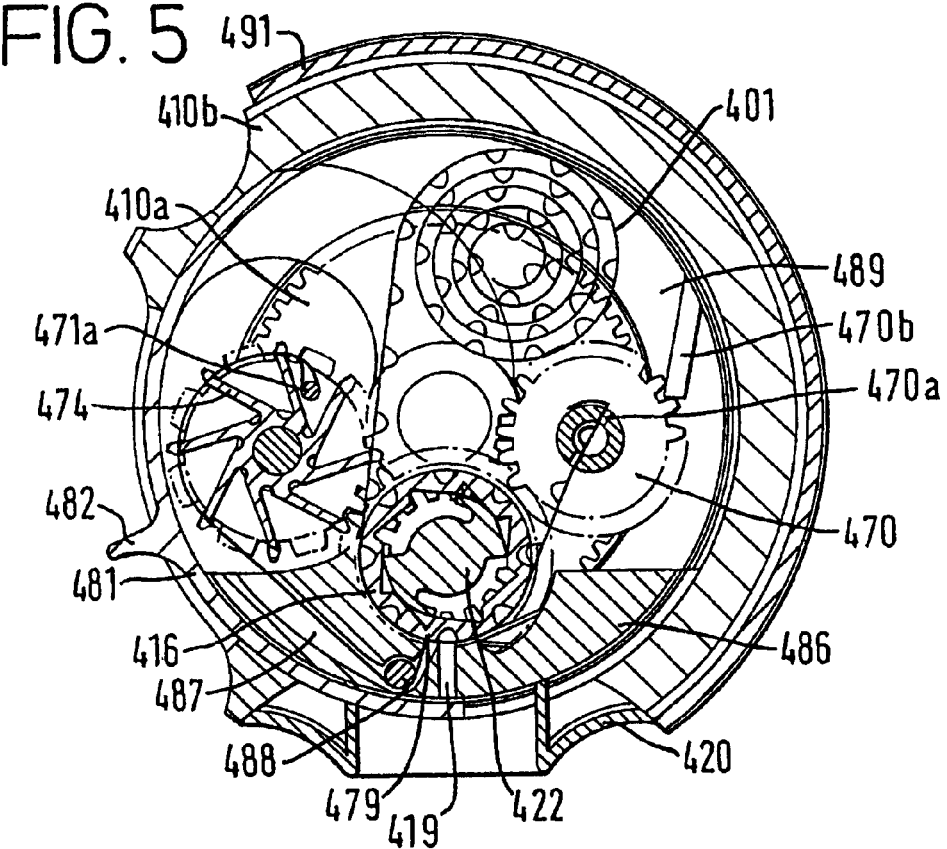
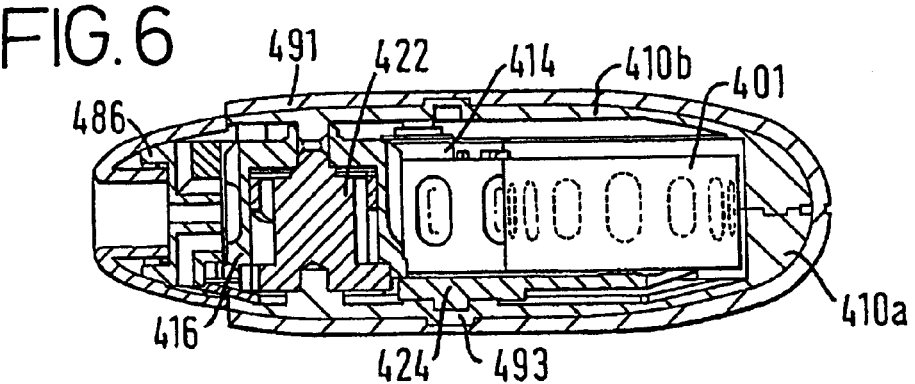

MEDICAMENT DISPENSER

CROSS-REFERENCE TO RELATED APPLICATIONS

This application is filed pursuant to 35 USC 371 as a United States National Phase Application of International Patent Application Serial No. PCT/EP2003/007937 filed on 17 Jul., 2003 which claims priority from GB 0216831.8 filed on 19 Jul. 2002 in the United Kingdom.

TECHNICAL FIELD

The present invention relates to a medicament dispenser for dispensing medicament. The invention particularly relates to a device for use in dispensing medicament in powder or tablet form.

BACKGROUND TO THE INVENTION

The use of inhalation devices in the administration of medicaments, for example in bronchodilation therapy is well known. Such devices generally comprise a body or housing within which a medicament carrier is located. Known inhalation devices include those in which the medicament carrier is a blister strip containing a number of discrete doses of powdered medicament. Such devices usually contain a mechanism of individually accessing these doses, usually comprising either piercing means or means to peel a lid sheet away from a base sheet. The powdered medicament can then be accessed and inhaled. Such a mechanism may also be used for dispensing medicament in tablet form wherein peeling away the lid sheet from the base sheet reveals a tablet for removal and subsequent consumption.

It is advantageous to provide the patient with a means for counting the number of doses of medicament dispensed or still remaining. It is desirable that any counting means be configured to register a count only when medicament is provided to the patient for inhalation, and in particular that opportunities for false counts and/or tampering are minimised. It is also desirable that the counting means be clearly visible by the patient and that the count be displayable in either analogue or digital form.

The Applicants have now devised various dose counting systems, which meet the some or all of the above criteria. In aspects, the counting systems may be provided to the medicament dispenser as a separable unit, which enables ready re-use and recycling thereof. The latter benefit is particularly important where the counter comprises electronic components, which are readily re-usable and potentially expensive to re-manufacture.

SUMMARY OF THE INVENTION

According to one aspect of the invention there is provided a medicament dispenser for use with a medicament carrier having multiple distinct medicament doses carried thereby, said dispenser having an internal mechanism for dispensing the distinct medicament doses carried by said medicament carrier, said mechanism comprising,
a) receiving means for receiving the medicament carrier;
b) release means for releasing a distinct medicament dose from the medicament carrier on receipt thereof by said receiving means;
c) an outlet, positioned to be in communication with the medicament dose releasable by said release means;
d) indexing means for individually indexing the distinct medicament doses of the medicament carrier; and
e) counting means for counting each time a distinct medicament dose of the medicament carrier is indexed by said indexing means, wherein said counting means is provided as a distinct electronic counter unit that is reversibly receivable by the medicament dispenser.

The medicament dispenser is shaped to receive an elongate form medicament carrier. Suitably, the elongate form medicament carrier is in the form of a strip or tape. The term medicament carrier is used to define any suitable carrier. In a preferred aspect, the carrier has a blister pack form, but it could also, for example, comprise a carrier onto which medicament has been applied by any suitable process including printing, painting and vacuum occlusion. The medicament carrier has multiple distinct (i.e. separate) medicament doses carried thereby.

The dispenser has an internal mechanism for dispensing the distinct medicament doses carried by the medicament carrier for administration for inhalation by the patient.

The mechanism comprises receiving means (e.g. a receiving station) for receiving the medicament carrier.

The mechanism further comprises release means for releasing a distinct medicament dose from the medicament carrier on its receipt by the receiving station. The release means can have any suitable form. Where the elongate carrier is in the form of a blister strip, the release means may for example, be a means to rupture or otherwise access the blister. In a particular preferred aspect, where the blister strip is peelably accessible, the release means comprises means for peeling apart the blister strip.

An outlet is positioned to be in communication with the distinct medicament doses releasable by said release means. The outlet may have any suitable form. In one aspect, it has the form of a mouthpiece and in another, it has the form of a nozzle for insertion into the nasal cavity of a patient.

The outlet is preferably a single outlet, which communicates with the distinct medicament dose releasable by said release means via a common air channelling means (e.g. formed as an air-pipe or common manifold). The patient may therefore breathe in through a single outlet, and that breath be transferred through the common channelling means to the released medicament dose, thereby enabling its inhalation. Baffles or other mechanical aids to break up released medicament powder may be incorporated. Venturi channelling of the air flow is also envisaged in embodiments. Helical form channels are envisaged.

The mechanism also comprises indexing means for individually indexing the distinct medicament doses carried by the medicament carrier. Said indexing typically happens in sequential fashion, for example accessing dose portions sequentially arranged along the length of the elongate carrier.

The medicament dispenser comprises counting means for counting each time a distinct medicament dose of the medicament carrier is indexed by said indexing means. Suitably, the indexing means and counting means engage (directly or indirectly e.g. via a coupling) with each other to enable counting of each indexation.

The counting means is provided as a distinct electronic counter unit, which is sized and shaped for reversible receipt by the medicament dispenser. The dispenser itself is typically adapted to for reversible receipt of the electronic counter unit (e.g. within a housing or a rotatable cover thereof).

The electronic counter unit typically comprises electronic circuitry and components such as a printed circuit board (PCB), a battery; an LCD screen; and is provided within a housing having a viewing window.

In one aspect, a housing or a rotatable cover of the medicament dispenser is provided with a cut-away portion (e.g. circular) shaped for reversible receipt of the electronic counter unit. Suitably, the electronic unit is provided with a housing shaped for socket receipt by the cut-away portion of the housing or cover of the medicament dispenser. Preferably, the electronic unit is receivable in reversible snap-fit fashion within the cut-away portion.

Suitably, the electronic counter unit is provided with (or communicates with) a display for displaying to the patient the number of distinct doses left to be taken or the number of doses taken.

In one aspect, the electronic counter unit is in switching contact with switching means coupled to the indexing means such that an indexing action results in switching thereof to register a count at the electronic counter unit. Suitably, the electronic counter unit is in switching contact with a mechanical arm, which protrudes from the body of the dispenser wherein said arm is coupled to the indexing means such that an indexing action (e.g. as a result of user movement of an index lever) results in switching movement thereof to actuate the electronic counter unit.

In another aspect, the electronic counter unit comprises an electronic reader capable of reading an analogue count indicium and displaying that indicium in electronic form on a display (e.g. an LCD screen). In one aspect, the analogue count indicium is displayed on an analogue (e.g. mechanical) counter provided to the medicament dispenser. In another aspect, the analogue count indicium is one of a series of count indicia applied to the medicament carrier (e.g. numbers printed on the side of an elongate blister strip).

In another aspect herein, the medicament dispenser is provided with an electronic counter unit incorporating a push-button actuation feature.

In aspects, the electronic counter unit is adapted to display further information of use to the patient. Thus information displayed can for example, include 'dose remaining', 'time since last dose', 'low dose warning', 'dose dispensed from device' and 'replacement dispenser needed'. In addition, visual or audible alarms may also be incorporated.

According to another aspect of the present invention the medicament dispenser is provided with means to manipulate, and in particular magnify, an analogue count indicium. The means may in one embodiment, comprise the hereinbefore described read-display unit. In another embodiment, the means comprises a prismatic viewer capable of acting on an indicium and causing it to be displayed in manipulated form at a desired viewing position.

Any or all components of the internal mechanism may be driven by either an electronic or mechanical drive system or combination thereof.

Suitably electronic drive means typically comprise a motor, preferably an electrically-powered motor. The motor may provide linear or rotary drive, but in general, rotary motors are most suitable. The motor may for example, comprise a DC electric motor, a piezoelectric (PZ) motor, an ultrasonic motor, a solenoid motor or a linear motor. Preferably, the electronic drive system comprises a DC motor, a PZ motor or an ultrasonic motor.

The use of ultrasonic motors is particularly preferred since they offer advantages over conventional motors in terms of weight, size, noise, cost and torque generated. Ultrasonic motors are well known in the art and are commercially available (e.g. BMSTU Technological Cooperation Centre Ltd, Moscow, Russia; Shinsei Corporation, Tokyo, Japan).

Ultrasonic motors do not use coils or magnets but comprise a piezo-electric ceramic stator which drives a coupled rotor. The stator generates ultrasonic vibrations which in turn causes rotation of the rotor. While regular DC motors are characterised by high speed and low torque, requiring reduction gearing to increase torque, ultrasonic motors attain low speed and high torque, thus eliminating the need for reduction gearing. Furthermore, these motors are lightweight and compact, lacking coils and magnets, and are noiseless as the ultrasonic frequencies used are not audible to the human ear.

Suitably, the dispenser further comprises actuating means for actuating said electronic drive system. Said actuating means may take the form of a switch, push-button, or lever.

In a preferred aspect, the medicament carrier comprises a peelable blister strip having a plurality of pockets for containing medicament wherein said pockets are spaced along the length of and defined between two peelable sheets secured to each other. The respective peelable sheets are generally in the form of a base sheet and a lid sheet of a pocket. In this aspect, the release means comprises peeling means for peeling apart a base sheet and lid sheet to open a pocket. Suitably, the peeling means includes lid driving means for pulling apart a lid sheet and a base sheet of a pocket that has been received at the opening station.

In one preferred aspect, there is provided a medicament dispenser for use with a medicament carrier having multiple distinct pockets for containing medicament doses, wherein said pockets are spaced along the length of and defined between two peelable sheets secured to each other, said dispenser having an internal mechanism for dispensing the medicament doses contained within said medicament carrier, said mechanism comprising, a) an opening station for receiving a pocket of the medicament carrier;

b) peeling means positioned to engage a base sheet and a lid sheet of a pocket which has been received in said opening station for peeling apart such a base sheet and lid sheet, to open such a pocket, said peeling means including lid driving means for pulling apart a lid sheet and a base sheet of a pocket that has been received at said opening station;

c) an outlet, positioned to be in communication with an opened pocket through which a user can access a medicament dose from such an opened pocket;

d) indexing means for individually indexing the distinct pockets of the medicament carrier; and e) counting means for counting each time a distinct medicament dose of the medicament carrier is indexed by said indexing means, wherein said counting means is provided as a distinct electronic counter unit that is reversibly receivable by the medicament dispenser.

Suitably, the indexing means comprises a rotatable index wheel having recesses therein, said index wheel being engageable with a medicament carrier in use with said medicament dispenser such that said recesses each receive a respective pocket of the base sheet of a blister strip in use with said medicament dispenser.

Suitably, the rotatable index wheel additionally comprises a series of indentations located at its base and spaced in between the recesses.

Suitably, the indexing means additionally comprises an interlock coupling to couple actuation of the dispenser to the index wheel. The interlock coupling reversibly locks the index wheel in place. Preferably, said interlock coupling comprises a foot portion having a toe and a heel, and a tail section. Preferably, said interlock coupling is pivotally mountable to the dispenser at its foot portion. Preferably, said toe fits into one of the indentations on the rotatable index wheel. Preferably, the interlock coupling is sprung to bias it towards location of the toe in one of the indentations.

Alternatively, the indexing means comprises a gear and sprocket wherein teeth on the wheel fit into apertures or holes formed on one or both edges of a medicament carrier. The mechanism therefore resembles that of photographic film being advanced through a camera.

Alternatively, the indexing means comprises an index ratchet which is moveable between a locked position whereby said ratchet engages a pocket on said medicament carrier and prevents further peeling thereof, and a release position allowing free movement of said medicament carrier. In this embodiment, actuation of said medicament dispenser actuates said lid driving means and releases said index ratchet from a medicament carrier to allow peeling thereof.

Suitably, said lid driving means comprises a wheel on which the lid sheet is wound up, said wheel having a winding surface which decreases in diameter when tension in the lid sheet increases. Preferably, said wheel comprises a plurality of resiliently flexible arms each extending therefrom at an angle with respect to a radius. The leading end of the lid sheet is looped over one of said resiliently flexible arms to secure the lid sheet to the wheel initially.

In one aspect, the lid driving means comprise a mangle. The lid sheet passes through two rotating wheels which act as a mangle and is gripped at the point of contact with the wheels. The used portion of the lid sheet is collected in a chamber after it has passed through the mangle.

In another aspect, the lid driving means comprise a roller. Preferably said roller is composed of a polymeric rubber and is positioned next to a guide wall. Preferably said roller has a smooth surface. Alternatively said roller has a knurled surface. The roller grips the lid sheet as it passes from the point at which it is separated from the base sheet through the space between the roller and the guide wall and the used portion of the lid sheet is then collected in a chamber. The roller has the advantage over the mangle described above in that a greater degree of contact between the roller wheel and the lid sheet occurs—the lid sheet is squeezed through the roller and may pass around about ⅓ of the roller wheel. This provides a higher level of grip and pulling force than with a mangle. The force required to turn the roller is constant throughout the use of the device and does not vary according to how much of the lid sheet has been peeled away from the base sheet. This is in contrast to the wheel described above where the forces required to turn the wheel may vary due to the fact that the lid sheet is wound around the wheel. The lid sheet is not wound around the roller. The roller also has the advantage that the lid sheet does not have to be looped around or fixed to the roller before use of the device, therefore simplifying assembly of the device and reducing costs.

In a further aspect, the lid driving means comprise a lid spool. The lid spool comprises a toothed wheel with a central upward cylindrical projection on which the lid sheet may be wound when it has been separated from the base sheet. The lid spool may have a mechanical gearing mechanism which is driven on actuation of the dispenser; the lid sheet is pulled away from the base sheet and wound onto the lid spool, causing the rotatable indexing wheel to turn and index the base sheet by one dose. An interlock coupling, as described supra, may be moved along the base of the rotatable indexing wheel until it fits into the next base recess. The positioning of the interlock coupling in this recess limits the movement of the lid spool to the distance between two pockets on the base sheet and therefore prevents the amount of lid sheet which is wound around the lid spool from increasing as the diameter of the lid spool is increased.

Suitably, said lid driving means comprises a wheel on which the lid sheet is wound up. Typically, said lid sheet wheel has an effective winding surface, the diameter of which increases after every use of the dispenser as the lid sheet winds around the wheel.

In order to ensure that the same dose is dispensed every time, that is, only a defined number of medicament pocket are opened for every actuation of the dispenser, there may be provided an electronic control system comprising means to limit the extent of movement of said lid driving means, in order to control the length of medicament carrier peeled by said peeling means. Hence, the medicament carrier is indexed by the same amount each time and a uniform, consistent dose is always dispensed.

The dispenser may further comprise compensating means positioned between said opening station and said lid sheet wheel for reducing the length of said lid sheet therebetween to compensate for any increase in the diameter of the effective winding surface of the lid sheet wheel during use of the dispenser.

Typically, the compensating means takes the form of a flexible member. The flexible member may take the form of a flexible elongate arm about which the lid sheet is fed. The arm may flex inwards as tension in the lid sheet increases, and thus shorten the length of lid sheet between the opening station and the lid driving means.

Suitably, the compensating means takes the form of a spring which reduces in length as tension increase in the lid sheet between the opening station and the lid driving means. Typically a piston head is mounted on one end of the spring about which the lid sheet is fed. The other end of the spring may be fixed. As tension in the lid sheet increases the piston is driven down onto the spring.

Suitably, the compensating means takes the form of a sprung-loaded tensioner.

Suitably, the flexible member is resilient so that on removal of tension from the lid sheet, the flexible member will return to its rest position. Thus, the internal mechanism can be reloaded with a new medicament carrier after the used carrier is removed.

Alternatively, or in addition, the dispenser may comprise a clutch means to adjust for any increase in the diameter of the effective winding surface of the lid driving means during use of the dispenser. In one aspect, the clutch means communicates with the indexing means and the lid driving means, and comprises a gearing surface defining plural gear engagement positions; and plural gear teeth for engaging said plural gear engagement positions, wherein the plural gear teeth are arranged such that at any one time only a single gear tooth engages a single gear engagement position.

It will be appreciated that, in use, the clutch means acts to compensate for the increase in diameter of said effective winding surface of the lid driving means. The clutch means allows for slippage when the tension in the lid sheet is greater than the force required to peel apart the lid sheet and the base sheet.

It will be appreciated that in total, the clutch means effectively defines a number of individual gear positions which is greater than the number of gear engagement positions. This is therefore advantageous over a traditional slipping clutch arrangement comprising intermeshing gear wheels, where the effective number of individual gear positions defined is either equal to, or no more than, the number of gear engagement positions defined by one of the gear wheels. The clutch means herein is also typically more compact than traditional slipping clutch arrangements e.g. because it enables smaller gearing surfaces to be employed.

Suitably, the gearing surface and plural gear teeth are arranged such that the number of individual gear positions defined is equal to the number of gear engagement positions multiplied by the number of gear teeth. In one example, if the gearing surface defines 60 gear engagement positions and there are 6 gear teeth, then up to 360 individual gear positions are definable (e.g. 1° resolution on a rotating gear system).

Suitably, the gearing surface defines from 20 to 100, preferably from 40 to 80 gear engagement positions. Suitably, the number of gear teeth is from 2 to 20, preferably from 3 to 10.

In one aspect, the gear engagement positions are equally spaced (e.g. equidistantly spaced) and the gear teeth are offset (e.g. non-equidistantly spaced) relative thereto. Such offset arrangement maximises the number of effective individual gear positions which are capable of definition. An example of this aspect, is a Vernier spring arrangement.

In another aspect, the gear engagement positions are also equally spaced (e.g. equidistantly spaced) and the gear teeth are located on a wobbling element capable of wobbling the gear teeth to plural offset (e.g. non-equidistantly spaced) positions. Such a wobbling offset arrangement also maximises the number of effective individual gear positions which are capable of being defined. An example of this aspect, is the wobbling wheel arrangement described herein.

In aspects, the clutch means is non-integral with either of the lid driving means or the indexing means, but forms a separate interconnecting component.

Suitably, the gearing surface comprises a gear wheel. As used herein, the term gear wheel encompasses, for example, a wheel, spindle or spool.

Suitably, the gear teeth may be arranged to be in ratchet form (i.e. enabling movement in one direction only).

Suitably, the gearing surface and gear teeth are in biased (e.g. sprung) engagement.

In one aspect, the lid driving means comprises a spiked wheel. As the spiked wheel turns, the lid sheet is pulled over it and the spikes perforate parts of the lid sheet to improve the grip on the lid sheet. The lid sheet then passes out into a chamber where it collects.

In another aspect, the lid driving means comprises a clamp system. The clamp system comprises at least one angled spring which is pivotable at one end and grips the lid sheet at the other end. The clamp system is moved in the direction that the lid sheet is to be pulled and grips the lid sheet, pulling it and therefore peeling it away from the base sheet. The clamp system is then moved back to its rest position. This results in the spring pivoting and clamping the lid sheet, therefore preventing the lid sheet from being further peeled from the base sheet.

In another aspect, the used portion of the lid sheet may be passed around rollers and fed back onto the used portion of the base sheet after the medicament has been accessed to join back onto the base sheet. The lid sheet may be coated with a sticky substance to aid resealing. The use of this mechanism saves space as the used portions of the blister strip will be collected in the same area.

In another aspect, the coil comprising an unused medicament carrier (e.g. blister strip) may be surrounded by a constant force spring. Alternatively, the coil comprising the unused blister strip may be surrounded by an elastomeric band or band comprising a contractible material. The constant force spring, elastomeric band or band comprising a contractible material contracts as the coil reduces in size.

Suitably, said peeling means additionally comprise a guide for guiding the lid sheet and base sheet along separate paths at the opening station. The lid sheet is passed around the guide portion onto the lid driving means.

Alternatively, the guide comprises a roller mechanism. The lid sheet is fed over the rollers onto the lid driving means.

Suitably, the internal mechanism additionally comprises a first chamber in which at least one strip is initially housed and from which it is dispensed and a second chamber to receive the used portion of the base sheet after it has been indexed around the index wheel and separated from the lid sheet.

Suitably, said first chamber and said second chamber are separated by a wall.

Suitably, said wall is movable to adjust the size of said first and second chambers.

In one aspect, the wall is pivotally mountable. Alternatively the wall is slidably mountable.

Suitably, the internal mechanism further comprises a third chamber to receive the used portion of the lid sheet and a fourth chamber which houses the index ratchet. The fourth chamber may communicate via a slit, which in turn extends upwardly within a mouthpiece and communicates with air inlets.

Suitably, the internal mechanism additionally comprises a crushing wheel to crush the medicament pockets after the medicament has been removed from them. The crushing wheel therefore reduces the space which the used portion of the base sheet takes up.

Typically, the internal mechanism for accessing said medicament contained within said medicament carrier is housed within a cassette.

Thus, in another embodiment, there is provided a medicament dispenser for dispensing medicament comprising: a body; a holder, shaped to fit within said body and movable relative to said body; and receivable by said holder, said cassette containing the medicament carrier.

Suitably, any electronic drive system is located in either the body or the holder part, and the cassette comprises the minimum number of component (i.e. internal mechanism) parts. In embodiments, the body/holder including the electronic drive is designed to be retained by the user and the cassette is sold as a refill/reload component which is discarded after use. By locating the electronic drive system in the body/holder, the amount of electronic components which are discarded is minimised which is advantageous from an environmental standpoint.

Suitably, the cassette of the medicament dispenser herein comprises a) an opening station for receiving a pocket of the medicament carrier;

b) peeling means positioned to engage a base sheet and a lid sheet of a pocket which has been received in said opening station for peeling apart such a base sheet and lid sheet, to open such a pocket, said peeling means including lid driving means for pulling apart a lid sheet and a base sheet of a pocket that has been received at said opening station;

c) an outlet, positioned to be in communication with an opened pocket through which a user can access a medicament dose from such an opened pocket; and d) indexing means for individually indexing the distinct pockets of the medicament carrier.

Suitably, movement of the holder relative to the body results in movement of the cassette between a first position and a second position such that the cassette is reversibly removable from the holder when the cassette is in the second position.

Suitably the first position comprises a dispensing position. Preferably the second position comprises a non-dispensing position. The cassette is therefore only removable from the holder when the cassette is in the non-dispensing position.

Suitably, the holder and body include attaching means to attach the holder to the body. Preferably, said attaching means comprise a snap fit mechanism. Suitably said snap fit mechanism comprises a pin and hole system.

Suitably, the holder is pivotally movable relative to the body. Alternatively the holder is rotationally movable relative to the body.

Suitably the holder additionally comprises a stop to limit movement of the holder relative to the body. The stop abuts against the edge of the body at two points when it is rotated. At these points the holder may be designed to click into place. Therefore when the stop abuts one body edge then it is clicked into the dispensing position and when the stop abuts the other body edge then it is clicked into the non-dispensing position.

Alternatively the holder is slidably movable relative to the body.

Suitably, the holder additionally comprises a catch to retain the cassette. The catch may for example comprise a sprung pin which fits into a hole or an integral catch which deforms when pressed allowing removal of the cassette.

Suitably, the catch is child resistant. Child resistance may be realised by having a system which forces the user to perform two actions at once to remove the cassette. Other features of the catch may include shock or impact resistance, the ability to lock the catch and orientation features to ensure that the cassette can only be inserted one way. The catch should also be easy to manufacture and assemble, be robust, be composed of a minimal number of components and intrude minimally into the space into which the cassette is inserted.

Suitably, the holder includes guide means to guide the cassette into the holder. Preferably said guide means comprise guide rails. Alternatively the guide means comprise grooves, indentations or other shaping or surface details to define a 'lock and key' relationship between the holder and the cassette. Colour guides, arrows and any other surface markings may also be employed.

Suitably, the cassette additionally comprises means to actuate the dispenser. The actuating means may take the form of a switch, push-button or lever.

Suitably, the cassette additionally comprises a mouthpiece.

Suitably, said mouthpiece is extendable. The mouthpiece extends as the cassette and holder are moved from the non-dispensing position to the dispensing position.

Alternatively the mouthpiece is retractable. The mouthpiece retracts as the cassette and holder are moved from the dispensing position to the non-dispensing position.

In one aspect, the mouthpiece is telescopic. In another aspect, the mouthpiece is fixed.

The medicament dispenser may also be designed for nasal inhalation of a powdered medicament and may therefore incorporate a nosepiece as an alternative to a mouthpiece. If the medicament is in solid form, the dispenser may incorporate an exit channel for tablet release.

Suitably, the body covers the mouthpiece and indexing means (e.g. lever) when the cassette is in the non-dispensing position. This avoids the need for a separate cover and protects the mouthpiece from the ingress of dirt and contaminants during storage.

Suitably, the cassette additionally comprises a raised portion to fit against the holder. The raised portion is located at the opposite end of the cassette to the mouthpiece/nosepiece/exit and indexing lever and prevents the incorrect insertion of the cassette into the holder since it is too wide to fit into the holder. The raised portion is shaped such that it fits against a cut away part of the holder. Preferably said raised portion includes a section which is raised to define a grip portion.

Suitably, at least a portion of the holder and body are shaped for ease of grip by the user.

Suitably, operation of the dispenser may be performed with one hand.

The dispenser may be assembled as follows. The holder is snap fitted into the body. The cassette is assembled separately. The body of the cassette is formed, preferably in two sections with any necessary spindles or integral components formed into the base. Individual components such as indexing wheels, lid winding mechanisms, guide portions etc are then assembled into the base. Finally the plural medicament containing blister strips (or other suitable elongate form medicament carriers) may be inserted into the cassette. These may be wound into the dispenser before the lid is attached to the cassette and the cassette sealed. Alternatively, the cassette may be formed completely apart from a hole left in its side for insertion of the plural blister strips or medicament carriers. The hole may then be sealed to complete the cassette. This second method of inserting the medicament carriers into the dispenser has the advantage that it is much simpler.

Suitably, the medicament dispenser additionally comprises an electronic data management system. The electronic data management system has input/output capability and comprises a memory for storage of data; a microprocessor for performing operations on said data; and a transmitter for transmitting a signal relating to the data or the outcome of an operation on the data.

Suitably, the electronic data management system is arranged to be responsive to or activated by the voice of a user. Thus, for example the system may be switched on or off in response to a voice command.

The electronic data management system may be integral with the body. Alternatively, the electronic data management system forms part of a base unit which is reversibly associable with the body.

Suitably, the medicament dispenser additionally comprises a data input system for user input of data to the electronic data management system. Preferably, the data input system comprises a man machine interface (MMI) preferably selected from a keypad, voice recognition interface, graphical user interface (GUI) or biometrics interface.

Energy may be conserved by a variety of means to enable the device to operate for longer on a given source of energy, such as a battery. Energy conservation or saving methods have additional advantages in terms of reducing the size requirements of the power source (e.g. battery) and thus the weight and portability of the medicament dispenser.

A variety of energy saving methods is available which generally involve reducing power consumption. One such method is to use a clock or timer circuit to switch the power on and off at regular or predetermined intervals. In another method the system can selectively switch on/off specific electronic devices, such as visual display units or sensors, in order to power these devices only when they are required to perform a particular sequence of events. Thus different electronic devices may be switched on and off at varying intervals and for varying periods under control of the system. The power sequencing system may also respond to a sensor, such as a motion or breath sensor, which is activated on use of the device.

Low power or "micropower" components should be used within the electronics where possible and if a high power device is required for a particular function this should be put into a low power standby mode or switched off when not required. Similar considerations apply in the selection of transducers. Operation at low voltage is desirable since power dissipation generally increases with voltage.

For low power digital applications complementary metal oxide semi-conductor (CMOS) devices are generally preferred and these may be specially selected by screening for low quiescent currents. Clock speeds of processors and other logic circuits should be reduced to the minimum required for computational throughput as power consumption increases with frequency. Supply voltages should also be kept at minimal values consistent with reliable operation because power dissipation in charging internal capacitance's during switching is proportional to the square of the voltage. Where possible, supply voltages should be approximately the same throughout the circuit to prevent current flowing through input protection circuits. Logic inputs should not be left floating and circuits should be arranged so that power consumption is minimised in the most usual logic output state. Slow logic transitions are undesirable because they can result in relatively large class-A currents flowing. Resistors may be incorporated in the power supply to individual devices in order to minimise current in the event of failure.

In some control applications, devices that switch between on and off states are preferred to those that allow analog (e.g. linear) control because less power is dissipated in low resistance on states and low current off states. Where linear components are used (e.g. certain types of voltage regulators) then types with low quiescent currents should be selected. In some circuit configurations it is preferable to use appropriate reactive components (i.e. inductors and capacitors) to reduce power dissipation in resistive components.

Suitably, the system additionally comprises a visual display unit for display of data from the electronic data management system to the user. The display may for example, comprise a screen such as an LED or LCD screen. More preferably the visual display unit is associable with the body of the medicament dispenser.

Suitably, the medicament dispenser additionally comprises a datalink for linking to a local data store to enable communication of data between the local data store and the electronic data management system. The datastore may also comprise data management, data analysis and data communication capability.

The datastore may itself form part of a portable device (e.g. a handheld device) or it may be sized and shaped to be accommodated within the patient's home. The datastore may also comprise a physical storage area for storage of replacement cassettes. The datastore may further comprise a system for refilling medicament from a reservoir of medicament product stored therewithin. The datastore may further comprise an electrical recharging system for recharging any electrical energy store on the medicament dispenser, particularly a battery recharging system.

The datalink may for example enable linking with a docking station, a personal computer, a network computer system or a set-top box by any suitable method including a hard-wired link, an infrared link or any other suitable wireless communications link.

Suitably, the medicament dispenser additionally comprises an actuation detector for detecting actuation of the dispensing mechanism wherein said actuation detector transmits actuation data to the electronic data management system.

The medicament dispenser may additionally comprise a safety mechanism to prevent unintended multiple actuations of the dispensing mechanism. The patient is thereby protected from inadvertently receiving multiple doses of medicament in a situation where they take a number of short rapid breaths. More preferably, the safety mechanism imposes a time delay between successive actuations of the release means. The time delay is typically of the order of from three to thirty seconds.

Suitably, the medicament dispenser additionally comprises a release detector for detecting release of medicament from the cassette, wherein said release detector transmits release data to the electronic data management system.

Suitably, the medicament dispenser additionally comprises a shake detector for detecting shaking of the medicament container (e.g. prior to actuation of the dispensing mechanism), wherein said shake detector transmits shake data to the electronic data management system.

Suitably, any actuation detector, release detector, or shake detector comprises a sensor for detecting any suitable parameter such as movement. Any suitable sensors are envisaged including the use of optical sensors. The release detector may sense any parameter affected by release of the medicament such as pressure, temperature, sound, moisture, carbon dioxide concentration and oxygen concentration.

Suitably, the medicament dispenser additionally comprises a breath trigger for triggering the dispensing mechanism, said breath trigger being actuable in response to a trigger signal from the electronic data management system. Preferably, the electronic data management system includes a predictive algorithm or look-up table for deriving from the breath data when to transmit the trigger signal. For example, a real-time analysis of the patient breath waveform may be made and the trigger point derived by reference to that analysed waveform.

Suitably, the electronic data management system includes a predictive algorithm or look-up table for calculating the optimum amount of medicament to dispense.

Suitably, the memory on the electronic data management system includes a dose memory for storing dosage data and reference is made to the dose memory in calculating the optimum amount of medicament to dispense.

Suitably, the medicament dispenser additionally comprises a selector for selecting the amount of medicament to dispense from said dispensing mechanism. In one aspect, the selector is manually operable. In another aspect, the selector is operable in response to a signal from the transmitter on the electronic data management system.

Suitably, the medicament dispenser comprises in association with a body or housing thereof, a first transceiver for transmitting and receiving data and in association with the medicament container, a second transceiver for transmitting and receiving data, wherein data is transferable in two-way fashion from the first transceiver to the second transceiver. The data is preferably in digital form and suitable for transfer by electronic or optical means. A medicament dispenser of this general type is described in pending UK Patent Application No. 0020538.5.

One advantage of embodiments of this type is the ability to store many types of information in different parts of the memory structure of the transceivers. The information is furthermore stored in a form which is readily and accurately transferable. The information could for example, include manufacturing and distribution compliance information written to the memory at various points in the manufacturing or distribution process, thereby providing a detailed and readily accessible product history of the dispenser. Such product history information may, for example, be referred to in the event of a product recall. The compliance information could, for example, include date and time stamps. The information could also include a unique serial number stored in encrypted form or in a password protectable part of the memory which uniquely identifies the product and therefore may assist in the detection and prevention of counterfeiting. The information could also include basic product information such as the nature of the medicament and dosing information, customer information such as the name of the intended customer, and distribution information such as the intended product destination.

On loading or reloading the medicament dispenser with a cassette the second transceiver may, for example, read the unique serial number, batch code and expiry date of the medicament and any other information on the second transceiver. In this way the nature and concentration of the medicament, together with the number of doses used or remaining within the cassette, may be determined. This information can be displayed to the patient on a visual display unit. Other information, such as the number of times the medicament dispenser has been reloaded with a cassette, may also be displayed.

Similarly, should the cassette be removed from the holder before the supply of medicament is exhausted, the same data can be read from the second transceiver and the number of doses remaining or used determined. Other information, such as the date and time of administration of the drug, or environmental exposure data such as the minimum/maximum temperatures or levels of humidity the cassette has been exposed to, may also be read and displayed to the user.

In the event that the supply of medicament within the container becomes exhausted, or that the shelf life of the medicament has expired, or that the first transceiver does not recognise the batch code on the second transceiver, activation of the dispenser may be prevented to safeguard the user. Activation may also be prevented if the medicament has been exposed to extreme environmental conditions for periods outwith the manufacturer's guidelines.

Data may be transferred to and from any transceiver during the period of use of the medicament dispenser by the patient. For example, the medicament dispenser may include an electronic data management system having various sensors associated therewith. Any data collected by the sensors or from any data collection system associated with the electronic data management system including a clock or other date/time recorder is transferable.

Data may be transferred each time the patient uses the device. Or alternatively, data may be stored in a database memory of the electronic data management system and periodically downloaded to any transceiver. In either case, a history of the usage of the device may be built up in the memory of a transceiver.

In one embodiment herein, a history of the usage of the medicament dispenser is transferred to the second transceiver. When the medicament carriers in the cassette are exhausted it is exchanged by the patient for a new refill cassette. At the point of exchange, which will typically occur at the pharmacy, data may be transferred from the exhausted cassette to the refill and vice-versa. Additionally, usage history data may be read from the refill and transferred to a healthcare data management system for example comprising a network computer system under the control of a healthcare data manager.

Methods are envisaged herein whereby the patient is given some sort of reward for returning the refill and making available the data comprised within the second transceiver. Methods are also envisaged herein whereby the healthcare data manager is charged for either receipt of the data from the second transceiver or for its use for commercial purposes. Any rewards or charging may be arranged electronically. The methods may be enabled by distributed or web-based computer network systems in which any collected data is accessible through a hub on the network. The hub may incorporate various security features to ensure patient confidentiality and to allow selective access to information collected dependent upon level of authorisation. The level of user authorisation may be allocated primarily to safeguard patient confidentiality. Beyond this the level of user authorisation may also be allocated on commercial terms with for example broader access to the database being authorised in return for larger commercial payments.

Suitably, the first and second transceiver each comprise an antenna or equivalent for transmitting or receiving data and connecting thereto a memory. The memory will typically comprise an integrated circuit chip. Either transceiver may be configured to have a memory structure which allows for large amounts of information to be stored thereon. The memory structure can be arranged such that parts of the memory are read-only, being programmed during/after manufacture, other parts are read/write and further parts are password protectable. Initial transfer of information (e.g. on manufacture or on dispensing) to or from any transceiver can be arranged to be readily achievable by the use of a reader which is remote from the medicament dispenser, thereby minimising the need for direct product handling. In further aspects, the reader can be arranged to simultaneously read or write to the memory of multiple transceivers on multiple medicament dispensers.

A suitable power source such as a battery, clockwork energy store, solar cell, fuel cell or kinetics-driven cell will be provided as required to any electronic component herein. The power source may be arranged to be rechargeable or reloadable.

Suitably, data is transferable in two-way fashion between the first and second transceiver without the need for direct physical contact therebetween. Preferably, data is transferable wirelessly between the first and second transceiver.

Suitably, the first transceiver is an active transceiver and the second transceiver is a passive transceiver. The term active is used to mean directly-powered and the term passive is used to mean indirectly-powered.

Suitably, the second transceiver comprises a label or tag comprising an antenna for transmitting or receiving energy; and an integrated circuit chip connecting with said antenna, and the first transceiver comprises a reader for said label or tag. In this case the label or tag is a passive transceiver and the reader is an active transceiver. Preferably, the reader will not need to be in direct contact with the tag or label to enable the tag or label to be read.

The tag may be used in combination and/or integrated with other traditional product labelling methods including visual text, machine-readable text, bar codes and dot codes.

Suitably, the integrated circuit chip has a read only memory area, a write only memory area, a read/write memory area or combinations thereof.

Suitably, the integrated circuit chip has a one-time programmable memory area. More preferably, the one-time programmable memory area contains a unique serial number.

Suitably, the integrated circuit chip has a preset memory area containing a factory preset, non-changeable, unique data item. The preset memory item is most preferably in encrypted form.

Suitably, the integrated circuit chip has plural memory areas thereon. Suitably, any memory area is password protected.

Suitably, any memory area contains data in encrypted form. Electronic methods of checking identity, error detection and data transfer may also be employed.

In one aspect, the integrated circuit has plural memory areas thereon including a read only memory area containing a unique serial number, which may for example be embedded at the time of manufacture; a read/write memory area which can be made read only once information has been written thereto; and a password protected memory area containing data in encrypted form which data may be of anti-counterfeiting utility.

Suitably, the tag is on a carrier and the carrier is mountable on the body or holder of the medicament dispenser or on the cassette.

In one aspect, the carrier is a flexible label. In another aspect, the carrier is a rigid disc. In a further aspect, the carrier is a rectangular block. In a further aspect, the carrier is a collar ring suitable for mounting to the neck of an aerosol container. Other shapes of carrier are also envisaged.

Suitably, the carrier is mouldable or weldable to the cassette or housing. Suitably, the carrier encases the tag. More preferably, the carrier forms a hermetic seal for the tag.

In one aspect, the carrier comprises an insulating material such as a glass material or, a paper material or an organic polymeric material such as polypropylene. Alternatively, the carrier comprises a ferrite material.

The energy may be in any suitable form including ultrasonic, infrared, radiofrequency, magnetic, optical and laser form. Any suitable channels may be used to channel the energy including fibre optic channels.

In one aspect, the second transceiver comprises a radiofrequency identifier comprising an antenna for transmitting or receiving radiofrequency energy; and an integrated circuit chip connecting with said antenna, and the first transceiver comprises a reader for said radiofrequency identifier. In this case the radiofrequency identifier is a passive transceiver and the reader is an active transceiver. An advantage of radiofrequency identifier technology is that the reader need not be in direct contact with the radiofrequency identifier tag or label to be read.

The radiofrequency identifier can be any known radiofrequency identifier. Such identifiers are sometimes known as radiofrequency transponders or radiofrequency identification (RFID) tags or labels. Suitable radiofrequency identifiers include those sold by Phillips Semiconductors of the Netherlands under the trade marks Hitag and Icode, those sold by Amtech Systems Corporation of the United States of America under the trade mark Intellitag, and those sold by Texas Instruments of the United States of America under the trade mark Tagit.

Suitably, the antenna of the RFID tag is capable of transmitting or receiving radiofrequency energy having a frequency of from 100 kHz to 2.5 GHz. Preferred operating frequencies are selected from 125 kHz, 13.56 MHz and 2.4 GHz.

In one aspect, the second transceiver comprises a magnetic label or tag comprising an antenna for transmitting or receiving magnetic field energy; and an integrated circuit chip connecting with said antenna, and the first transceiver comprises a reader for said magnetic label or tag. In this case the magnetic label or tag is a passive transceiver and the reader is an active transceiver.

A suitable magnetic label or tag comprises plural magnetic elements in mutual association whereby the magnetic elements move relative to each other in response to an interrogating magnetic field. A magnetic label or tag of this type is described in U.S. Pat. No. 4,940,966. Another suitable magnetic label or tag comprises a magnetorestrictive element which is readable by application of an interrogating alternating magnetic field in the presence of a magnetic bias field which results in resonance of the magnetorestrictive elements at different predetermined frequencies. A magnetic label of this type is described in PCT Patent Application No. WO92/12402. Another suitable magnetic label or tag comprising plural discrete magnetically active regions in a linear array is described in PCT Patent Application No. WO96/31790. Suitable magnetic labels and tags include those making use of Programmable Magnetic Resonance (PMR) (trade name) technology.

In another aspect, the second transceiver comprises a microelectronic memory chip and the first transceiver comprises a reader for said microelectronic memory chip. The microelectronic memory chip may comprise an Electrically Erasable Programmable Read Only Memory (EEPROM) chip or a SIM card-type memory chip. In this case the microelectronic memory chip is a passive transceiver and the reader is an active transceiver.

Any transceiver herein, particularly a passive transceiver may be mounted on or encased within any suitable inert carrier. The carrier may comprise a flexible sheet which may in embodiments be capable of receiving printed text thereon.

In one aspect, the first transceiver is integral with the body such that a single unit is comprised. The first transceiver may for example be encased within or moulded to the body.

In another aspect, the first transceiver forms part of a base unit which is reversibly associable with the body. The base unit may for example, form a module receivable by the body such as a snap-in module.

Suitably, the medicament dispenser additionally comprises a communicator for wireless communication with a network computer system to enable transfer of data between the network computer system and the electronic data management system. Dispensers employing such communicators are described in pending PCT Applications No.s PCT/EP00/09291 (PG3786), PCT/EP00/09293 (PG4029) and PCT/EP00/09292 (PG4159). Preferably, the communicator enables two-way transfer of data between the network computer system and the electronic data management system.

Suitably, the data is communicable between the network computer system and the electronic data management system in encrypted form. All suitable methods of encryption or partial encryption are envisaged. Password protection may also be employed. Suitably, the communicator employs radiofrequency or optical signals.

In one aspect, the communicator communicates via a gateway to the network computer system. In another aspect, the communicator includes a network server (e.g. a web server) such that it may directly communicate with the network.

In a further aspect, the communicator communicates with the gateway via a second communications device. Preferably, the second communications device is a telecommunications device, more preferably a cellular phone or pager. Preferably, the communicator communicates with the second communications device using spread spectrum radiofrequency signals. A suitable spread spectrum protocol is the Bluetooth (trade mark) standard which employs rapid (e.g. 1600 times a second) hopping between plural frequencies (e.g. 79 different frequencies). The protocol may further employ multiple sending of data bits (e.g. sending in triplicate) to reduce interference.

In one aspect, the network computer system comprises a public access network computer system. The Internet is one suitable example of a public access network computer system, wherein the point of access thereto can be any suitable entrypoint including an entrypoint managed by an Internet service provider. The public access network computer system may also form part of a telecommunications system, which may itself be either a traditional copper wire system, a cellular system or an optical network.

In another aspect, the network computer system comprises a private access network computer system. The private access network system may for example, comprise an Intranet or Extranet which may for example, be maintained by a health service provider or medicament manufacturer. The network may for example include password protection; a firewall; and suitable encryption means.

Preferably, the communicator enables communication with a user-specific network address in the network computer system.

The user-specific network address may be selected from the group consisting of a web-site address, an e-mail address and a file transfer protocol address. Preferably, the user-specific network address is accessible to a remote information source such that information from said remote information source can be made available thereto. More preferably, information from the user-specific network address can be made available to the remote information source.

In one aspect, the remote information source is a medicament prescriber, for example a doctors practice. Information transferred from the medicament prescriber may thus, comprise changes to prescription details, automatic prescription updates or training information. Information transferred to the medicament prescriber may comprise compliance information, that is to say information relating to the patient's compliance with a set prescribing programme. Patient performance information relating for example, to patient-collected diagnostic data may also be transferred to the medicament prescriber. Where the dispenser is an inhaler for dispensing medicament for the relief of respiratory disorders examples of such diagnostic data would include breath cycle data or peak flow data.

In another aspect, the remote information source is a pharmacy. Information transferred from the pharmacy may thus, comprise information relating to the medicament product. Information sent to the pharmacy may thus include prescription requests which have been remotely pre-authorised by the medicament prescriber.

In a further aspect, the remote information source is an emergency assistance provider, for example a hospital accident and emergency service or an emergency helpline or switchboard. The information may thus, comprise a distress or emergency assist signal which requests emergency assistance.

In a further aspect, the remote information source is a manufacturer of medicament or medicament delivery systems. Information transferred to the system may thus, comprise product update information. The system may also be configured to feed information back to the manufacturer relating to system performance.

In a further aspect, the remote information source is a research establishment. In a clinical trial situation, information may thus be transferred relating to the trial protocol and information relating to patient compliance fed back to the research establishment.

In a further aspect, the remote information source is an environmental monitoring station. Information relating to weather, pollen counts and pollution levels may thus be made accessible to the system.

Suitably, the medicament dispenser additionally comprises a geographic positioning system such as a global positioning system or a system which relies on the use of multiple communications signals and a triangulation algorithm.

Suitably the medicaments are selected from the group consisting of albuterol, salmeterol, fluticasone propionate and beclomethasone dipropionate and salts or solvates thereof. Preferably, the combination comprises salmeterol xinafoate and fluticasone propionate.

According to another aspect of the present invention there is provided the medicament dispenser described above in kit of parts form. A first part of the kit comprises a body; a holder, shaped to fit within said body and movable relative to said body; and within said holder a receiving station for receipt of a cassette. A second part of the kit comprises a cassette containing an elongate form medicament carrier and an internal mechanism for indexing said elongate form medicament carrier, wherein the cassette is receivable by the receiving station and movement of the holder relative to the body results in movement of the cassette between a first position and a second position such that the cassette is reversibly removable from the receiving station when the cassette is in the second position.

In one aspect, the medicament dispenser may be assembled as follows. The holder is snap fitted into the body. The cassette is assembled separately. The body of the cassette is formed, preferably in two sections with any necessary spindles or integral components formed into the base. Individual components such as indexing wheels, lid winding mechanisms, guide portions etc are then assembled into the base. Finally the elongate form medicament carrier (e.g. blister strip) is inserted into the cassette. This may be wound into the dispenser before the lid is attached to the cassette and the cassette sealed. Alternatively, the cassette may be formed completely apart from a hole left in its side for insertion of the medicament carrier. The hole may then be sealed to complete the cassette. This second method of inserting the medicament carrier into the device has the advantage that it is much simpler.

BRIEF DESCRIPTION OF THE DRAWINGS

The invention will now be described with reference to the accompanying drawings in which:

FIGS. 4 to 7 show a medicament dispenser suitable for adaptation in accord with the present invention: FIG. 4 being an underplan view; FIG. 5 a section on line A—A in FIG. 4; FIG. 6 a section on line B—B in FIG. 4; and FIG. 7 an exploded view on a smaller scale;

FIG. 7e is a section taken on line A—A in FIG. 7a;

DETAILED DESCRIPTION OF THE DRAWINGS

Figure 1:
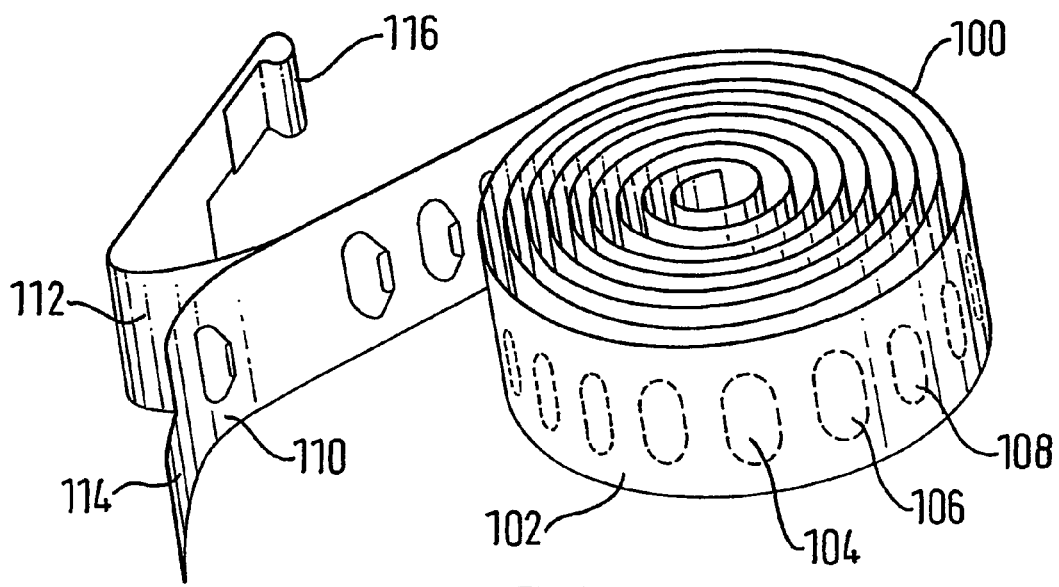
FIG. 1 shows a perspective view of a medicament carrier suitable for use in accord with the present invention.

FIG. 1 shows a medicament carrier 100 for use in accord with the present invention. The medicament carrier comprises a flexible strip 102 defining a plurality of pockets 104, 106, 108 each of which would contain a portion of a dose of medicament which can be inhaled, in the form of powder. Herein, plural such strips 102 would be employed in a single medicament dispenser, wherein each strip comprises individual blister-sealed doses of a medicament product.

The strip comprises a base sheet 110 in which blisters are formed to define the pockets 104, 106, 108 and a lid sheet 112 which is hermetically sealed to the base sheet except in the region of the blisters in such a manner that the lid sheet 112 and the base sheet 110 can be peeled apart. The sheets 110, 112 are sealed to one another over their whole width except for the leading end portions 114, 116 where they are preferably not sealed to one another at all. The lid 112 and base 110 sheets are each preferably formed of a plastics/aluminium laminate and are preferably adhered to one another by heat sealing.

The strip 102 is shown as having elongate pockets 104, 106, 108 which run transversely with respect to the length of the strip 102. This is convenient in that it enables a large number of pockets 104, 106, 108 to be provided in a given strip 102 length. The strip 102 may, for example, be provided with sixty or one hundred pockets but it will be understood that the strip 102 may have any suitable number of pockets.

Figure 2:
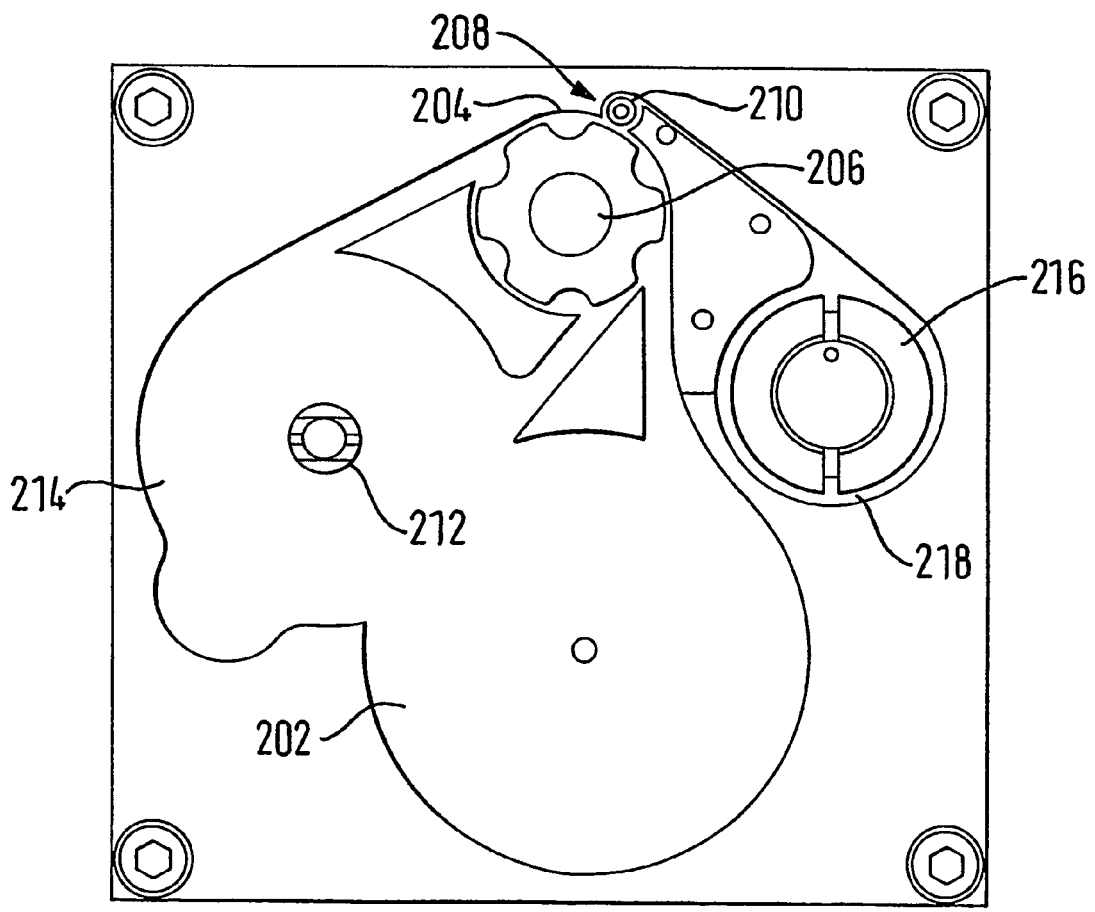
FIG. 2 shows a base unit housing an internal mechanism suitable for adaptation in accordance with one aspect of the invention.

FIG. 2 illustrates a base unit 200 of a prior art medicament dispenser suitable for adaptation in accord with the present invention. A blister strip (not shown for clarity) is positioned in chamber 202 of the base unit 200. The blisters strip are pre-fed through a guide member 204 within the manifold component and engaged in a six-pocket index wheel 206. The first pocket of each blister strip is positioned one pocket away from the opening station 208. The lid foil and base foil are separable about a beak 210. The resulting empty base foil is coiled about a base take-up spindle 212 in the base take-up chamber 214. The used lid foil is fed over the beak 210 and coiled about a lid take-up spindle 216 in the lid take-up chamber 218.

The dispenser is actuated by pressing a button on the side of the dispenser (not shown) to index the internal mechanism by one pocket of medicament. Initially, the gearing between the index wheel 206 and the lid take-up foil spindle 216 is one-to-one. However, as the lid take up spindle 216 winds on more foil, its effective winding diameter increases. An increase in diameter would cause the lid take-up spindle 216 to pull more strip than the index wheel 206 releases.

Figure 3:
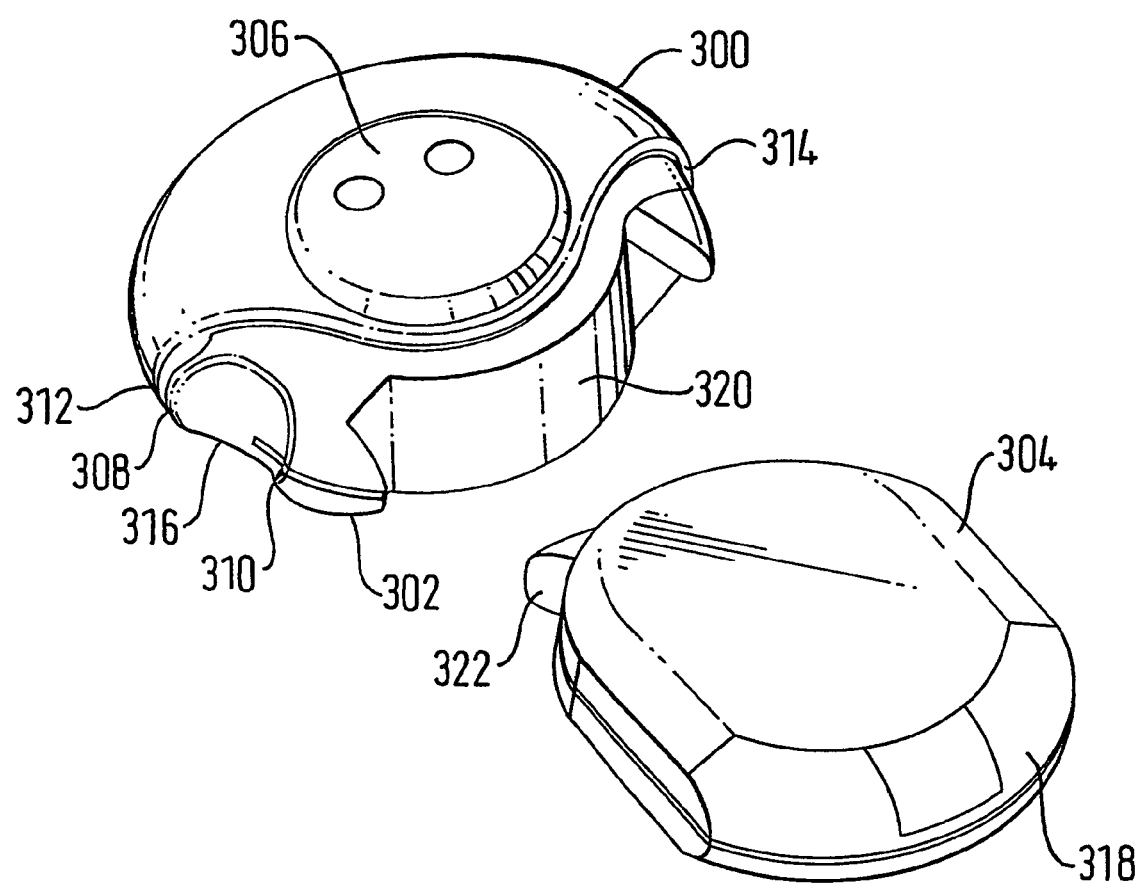
FIG. 3 shows a perspective view of a medicament dispenser, in the form of a holder/body and a refill cassette, for use in accord with the invention with the cassette removed from the holder/body.

FIG. 3 shows a prior art medicament dispenser of a form suitable for adaptation in accord with the present invention, comprising a body 300, a holder 302, refill cassette 304 and electronic display 306. The holder 302 is shaped to fit snugly inside body 300 and is fixed to a point on the body (not shown) about which it rotates. Stops 308, 310 protrude from the holder 302 and prevent the holder 302 from rotating more than about 180° relative to the body 300. The stops 308, 310 also provide two defined positions of the holder 302 within the body 300. One position is defined by stop 308 meeting with body edge 312 and the other position defined by stop 310 meeting with body edge 314 when the holder has been rotated relative to the body. The area between stops 308 and 310 is shaped to form a thumb or finger grip 316 for the user of the device. The holder 302 forms a shell into which the refill cassette 304 snugly fits.

The refill cassette 304 comprises a shell containing the plural medicaments carrier (not shown) and a mechanism for opening the carriers (not shown) for the medicament to be accessed. The refill cassette 304 has a raised portion 318 at one end on both sides along its width so that this part of the refill cassette 304 is at least the same depth as the part of the holder 320 which receives the refill cassette 304. This allows the position of the cassette 304 within the holder 302 to be fixed such that the ridge 318 protrudes from the holder 302 but the rest of the cassette 304 is contained within the holder 302.

The refill cassette 304 also has a mouthpiece (not shown) and an actuating push button 322 for actuating the device to index the medicament carrier within the cassette 304.

FIGS. 4 to 7 show a prior art device, which is suitable for adaptation in accord with the present invention. As in the first embodiment, the device receives a flexible strip, here denoted as 401, comprising a base sheet 403 in which pockets 402 are defined and a lid sheet 404. The strip 401, is shown most clearly in FIG. 1. The lid sheet 404 has a loop 404a formed at the leading end thereof for engagement over a post 471a extending upwardly from a toothed wheel 471 (described below). The base sheet has a lead portion 403a of reduced width for engagement in a slot 470a formed in the base winding wheel 470 (described below). The leading end portions of the base sheet and lid sheet are not sealed together, as can be seen in FIG. 4.

The body 410 comprises a base 410a and a top 410b both of generally circular shape. When the device is assembled the base and top are snap-fitted together. The body defines a single internal chamber within which the strip 401 is housed and within which are also housed a wheel 414 for winding up the used portion of the lid sheet 404, a base winding wheel 470 and an index wheel 416. The index wheel 416 is hollow and an index ratchet wheel 422 is housed within it. All the wheels just mentioned are mounted in the chamber defined by the body, for rotational movement with respect thereto. A pawl 470b is attached to the body 410 and engages the teeth of the base winding wheel 470 to prevent the wheel moving anticlockwise, thus ensuring that the strip 401 can only proceed forwards through the device.

The lid winding wheel 414 is formed in two parts, namely a toothed wheel 471 having teeth 472 and a shaft 473, and a collapsible wheel 474 having a hollow central shaft 475 and a plurality of resilient arms 476, for example, as shown, eight such arms, extending from the central shaft 475 each at an angle to a radius. The toothed wheel 471 has a lug 477 which engages in a corresponding notch in the shaft 475 so that the wheels 471 and 474 rotate in unison.

The hollow index wheel 416 has external teeth 478 which mesh with the teeth of the base winding wheel 470 and the teeth of the wheel 471. Ratchet teeth 479 are formed on the internal walls of the index wheel 416, and the index ratchet wheel 422 has two pawls 480 which engage the ratchet teeth 479.

The device further comprises a lever 424 which comprises an arcuate wall 481 with a finger tab 482, and an arm 483 which extends inwardly from the wall 481 and carries an arcuate array of teeth 484 at its distal end. The lever is pivotally mounted to the centre of the base 410a for movement about an axis which is at the centre of the pitch circle of the teeth 484, the teeth 484 mesh with the teeth 485 on the index ratchet wheel 422.

A manifold 486 provides communication between the chamber within the body 410 and a mouthpiece 420. The manifold has a powder outlet 419 and also has a passageway 487 to allow used lid strip 404 to pass to the collapsible wheel 474. Optionally, a roller 488 may be provided to guide the strip 404 into the passageway 487.

A dose monitor ring 489 having teeth 490 is arranged to be rotatable within the body base 410a. On its lower surface this bears indicia (not visible in the drawings) which can be viewed by the user through a window 494 in the body 410. It will be noted from FIGS. 7a to 7d that the window can be seen both when the cover 491 (see below) is closed and when it is open. The indicia indicate either exactly or approximately the number of doses left (or the number of doses used, if preferred). The ring 489 is rotated by virtue of the fact that its teeth 490 are engaged by the teeth 478 of the index wheel.

The device is provided under a cover 491 which is pivotally mounted on the body 410 by means of a lug 492 on the body top 410b and a corresponding lug 493 on the body base 410a. The cover is pivotal between an open position (shown in FIG. 5) in which the mouthpiece is exposed and a closed position in which it is not, as is described more fully below.

In operation, the user moves the cover 491 to its open position and then presses on the finger tab 482 of the lever 424 to cause it to move as the lever pivots. This makes the index ratchet wheel 422 rotate which, via the pawls 480, causes the index wheel 416 also to rotate. Rotation of the index wheel 416 produces rotation of both the base winding wheel 470 and the lid winding wheel 414, thus peeling the base sheet and lid sheet apart over a distance sufficient to expose a previously unopened pocket 402 opposite the end of the powder outlet 419 in the manifold. The patient can then inhale through the mouthpiece, as in the preceding embodiments.

Figure 7:
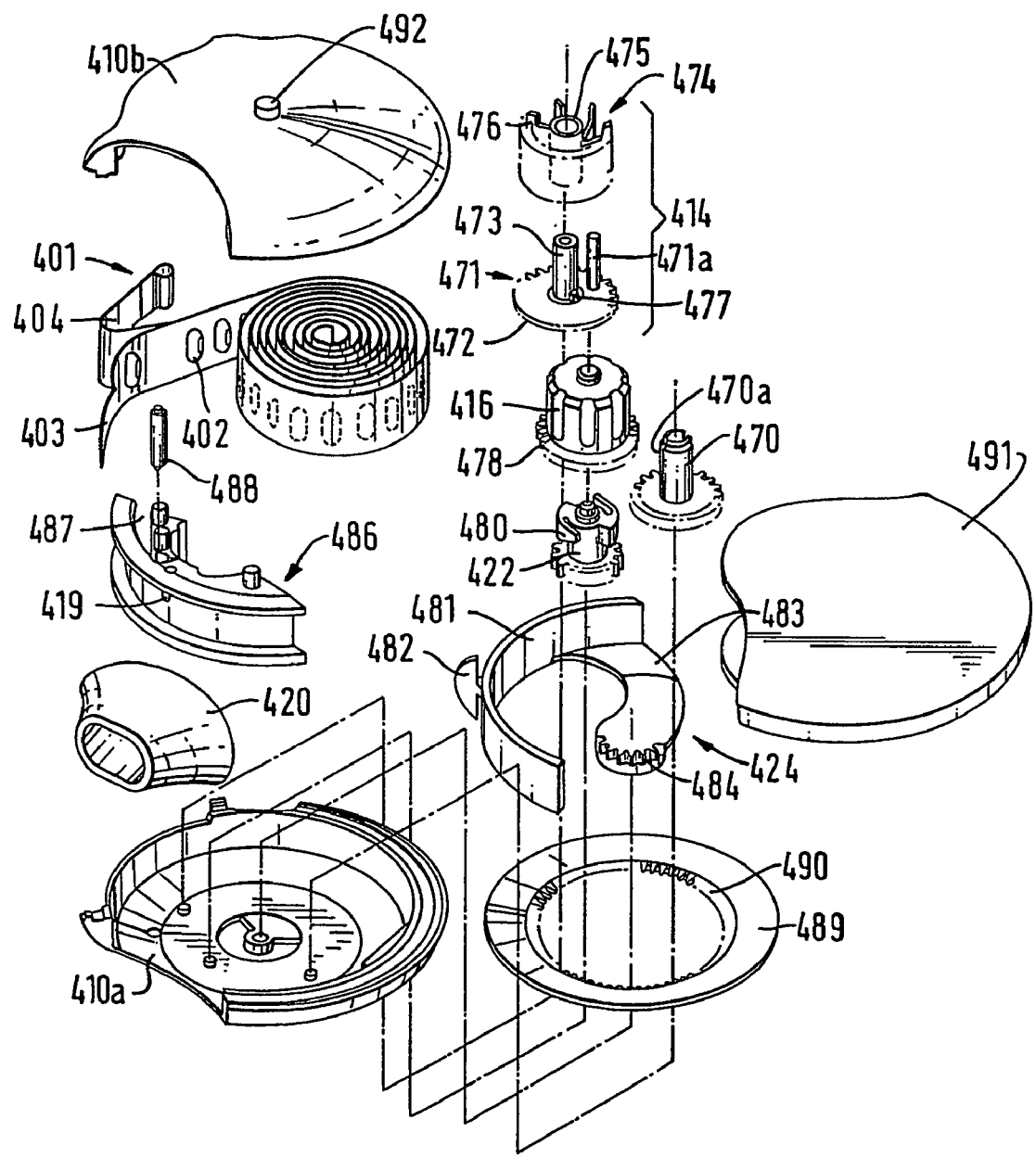
Figure 7A:
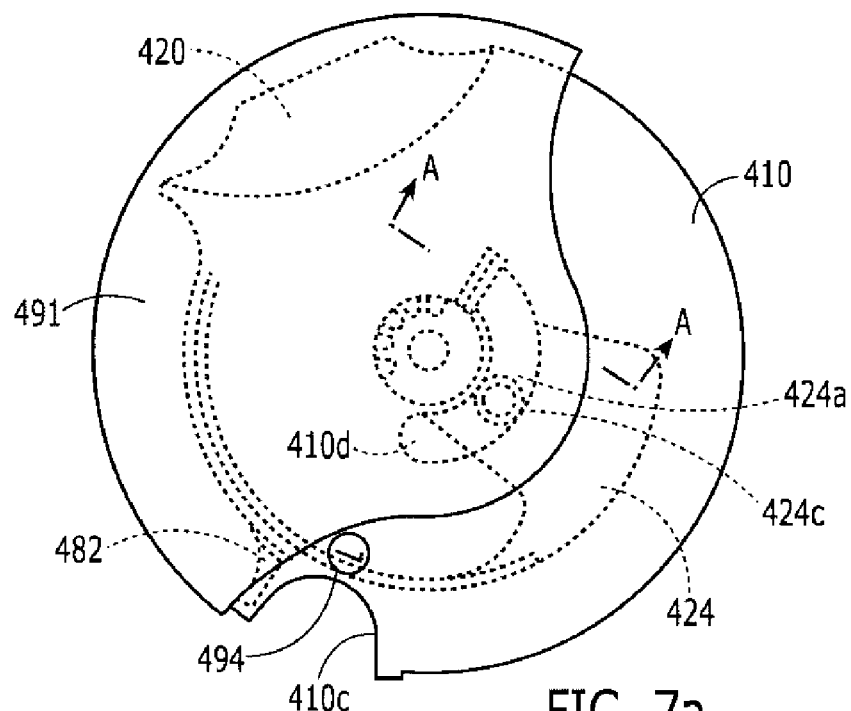
FIGS. 7a to 7d show the embodiment of FIGS. 4 to 7 in successive stages of operation.
Figure 7B:
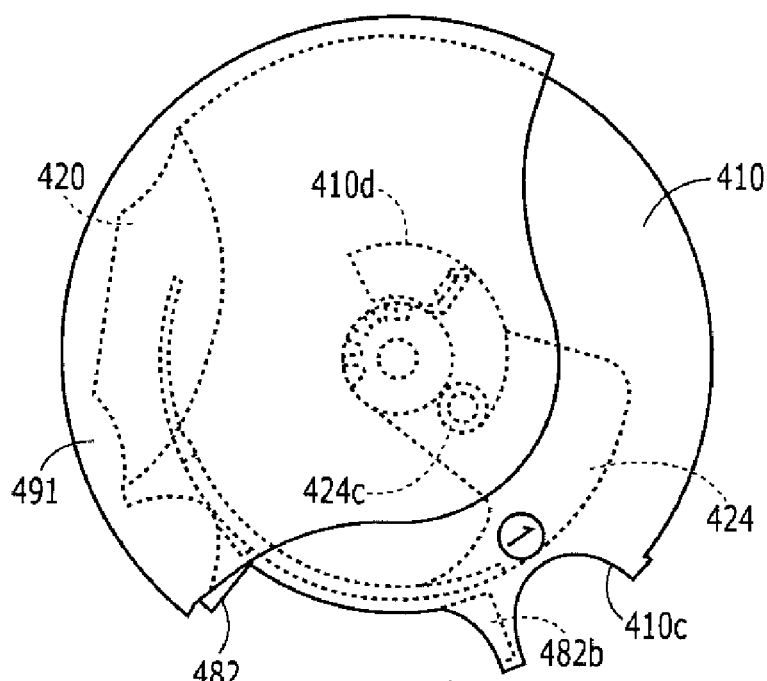

Successive stages in the operation of the device are shown in FIGS. 7a to 7d. FIG. 7e is a section taken on line A—A in FIG. 7a. The device is in its closed position in FIGS. 7a and 7e. The finger tab 482 of the lever 424 is at this stage in a recess 482b formed in the body 410 (seen more clearly in FIGS. 7b and 7c). The cover 419 is held stationary as the body 410 is rotated anticlockwise, a recess 410c being provided in the periphery of the body to enable the user to insert a finger for this purpose. The device is thus moved to the partly open position shown in FIG. 7b. During this process the lever 424 remains stationary with respect to the cover 491. This is achieved by the lever being provided internally with a resilient arm 424a the tip 424b of which engages in a recess 491a in the cover 491. The arm 424a is attached to the lever 424 via a cylindrical member 424c. As viewed in FIG. 7a, the arm 424a extends anticlockwise from the member 424c over an arc of about 90.degree. The cylindrical member 424c is guided in an arcuate slot 410d formed in the body 410. The slot 410d extends through an arc of about 180.degree, and in FIGS. 7a and 7e the member 424c is shown as being approximately half way along its length. In FIG. 7b it is shown as being at one end.

Figure 7C:
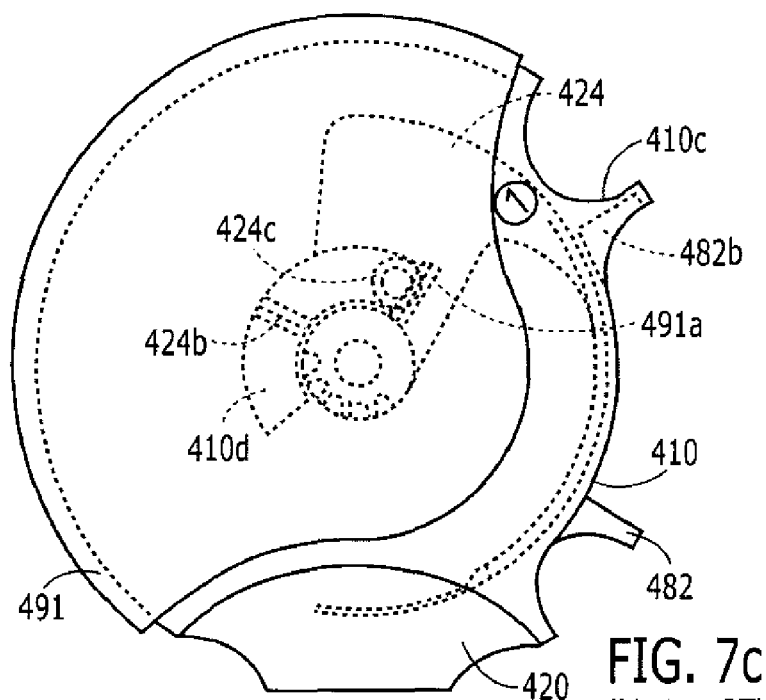
Figure 7D:
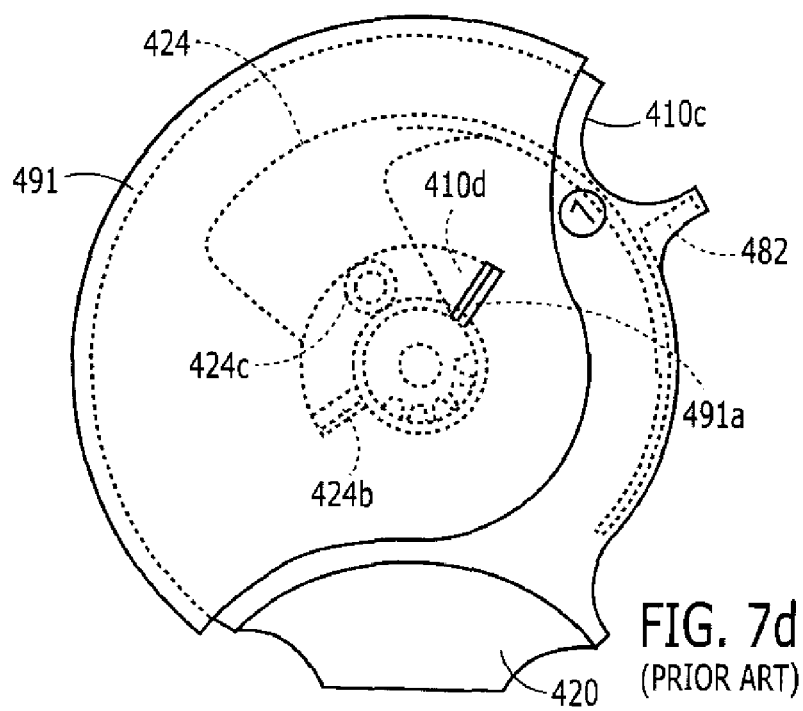
Figure 7E:
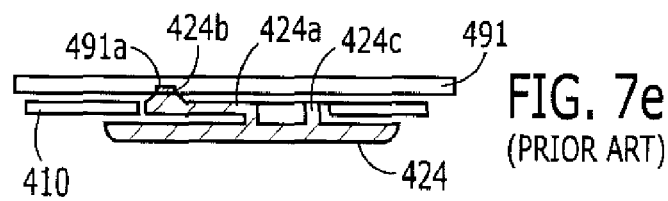

The user continues to rotate the body 410 from the position shown in FIG. 7b to the position shown in FIG. 7c. During this further rotation tip 424b of the arm 424a jumps out of the recess 491a. This occurs because, with the member 424c at one end of the slot 410d, movement of the body 410 carries the member 424c with it in an anticlockwise direction and hence compels the arm 424a likewise to move anticlockwise. The user then moves the lever 424 by pushing on the finger tab 482 to cause it to rotate anticlockwise through the position shown in FIG. 7c to the position shown in FIG. 7d where the finger tab 482 re-enters the recess 482b. The steps thus far described both expose the mouthpiece 420 and open a fresh blister. The device is therefore now ready for the user to inhale.

After use, the body 410 is rotated clockwise, the lever 424 moving in unison with the body, to bring the device back to the position of FIGS. 7a and 7e.

It will be noted that the collapsible wheel 474 in effect assumes the function of a clutch. As more lid sheet is wound onto the wheel 474 the arms 476 gradually flex inwardly, and the effect is to keep the external diameter of the reel of wound up lid sheet substantially constant, while the internal diameter thereof gradually decreases.

Figure 8A:
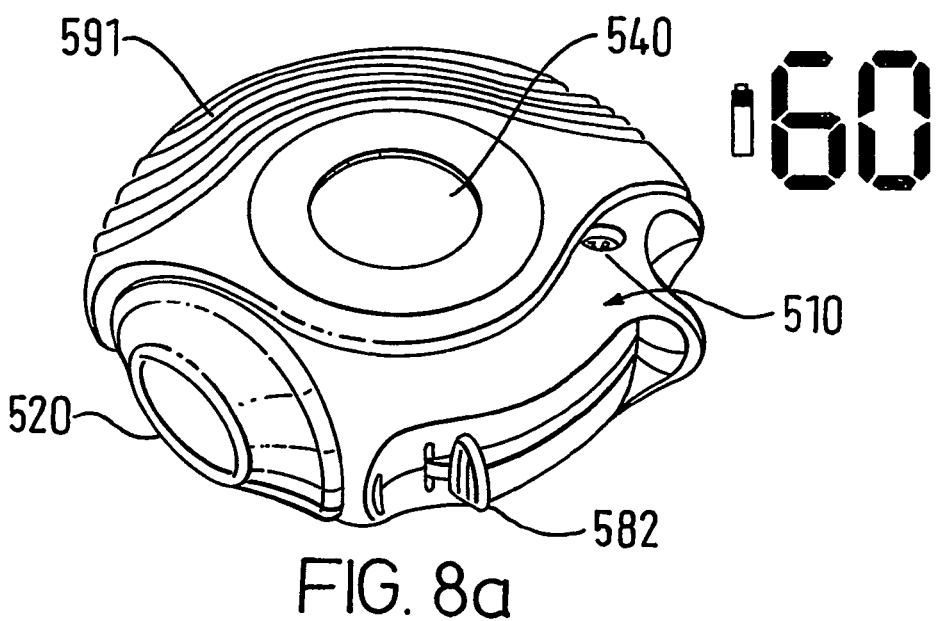
FIGS. 8a and 8b respectively show in plan and exploded view, a medicament dispenser having an electronic counter in accord with one aspect of the present invention.
Figure 8B:
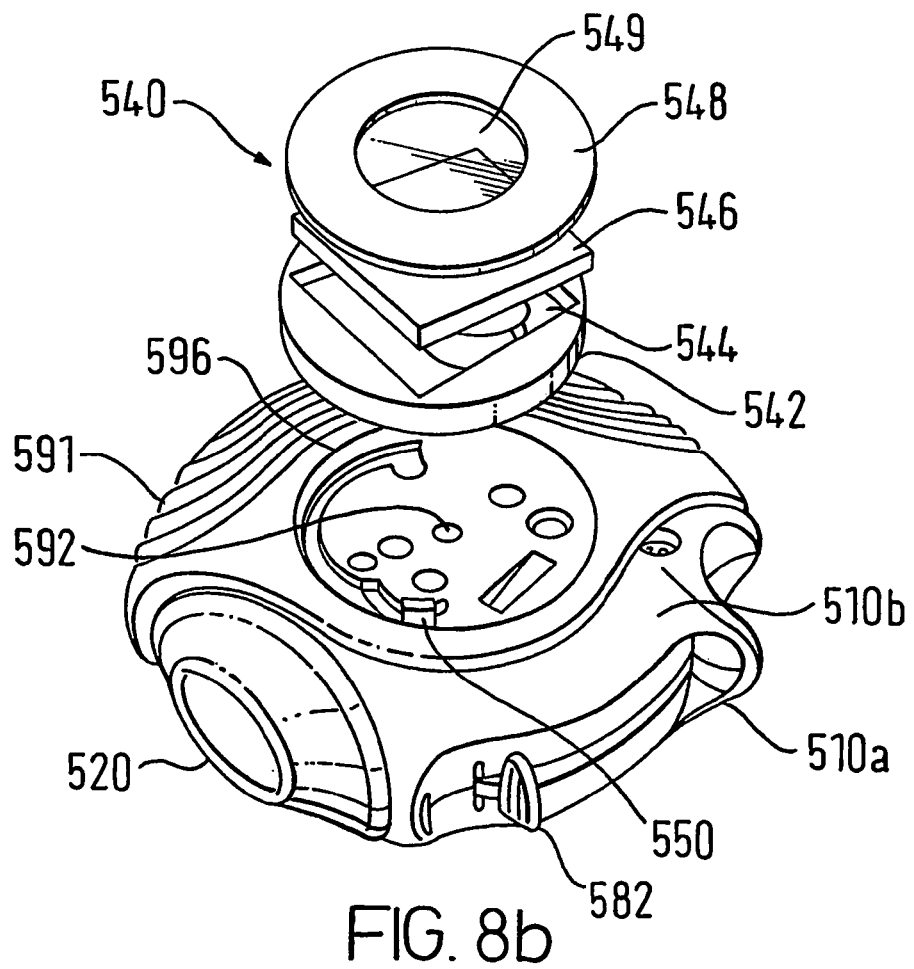

FIG. 8 shows in exploded view, a medicament dispenser that may be formed by suitable adaptation of the dispenser of FIGS. 4 to 7d. Thus, the dispenser is provided under a cover 591, which is pivotally mounted to body 510 by means of a lug 592 on the body top 510b and (not visible) a corresponding lug on the body base 510a. The cover 591 is pivotable between an open position (shown in FIG. 8a) in which the mouthpiece 520 is exposed and a closed position in which it is not.

The cover 591 is provided with a circular cut-away portion 596 shaped for receipt of a detachable electronic dose counter unit 540, which comprises an electronics housing 542 shaped for socket receipt by the cut-away portion 596 of the cover 591; a battery 544; an LCD screen with integral microprocessor chip 546; and a protective cover 548 having a viewing window 549 provided thereto. In a preferred aspect, the electronic counter unit 540 is received in snap-fit fashion within the cut-away portion 596 of the cover 591.

Actuation of the electronic dose counter 540 to register a count is by switching engagement with a notch element 550, which protrudes from the body top 510b. The notch element 550 is movable in response to movement of the finger tab indexer 582 whose primary function is to advance the dose indexing mechanism within the device (see earlier description of FIGS. 4 to 7d). As the tab 582 is actuated therefore, both the dose is indexed and that indexing action is registered by the counter unit 540.

In more detail, in operation, the user moves the cover 591 to its open position and then presses on the finger tab 582 to cause it to move. This results both in indexing of the medicament dose and movement of the notch element 550, which engages the counter unit 540 thereby causing a count to be registered. The patient then inhales through the mouthpiece 520 to access the medicament dose, as in the preceding embodiments.

Figure 9A:
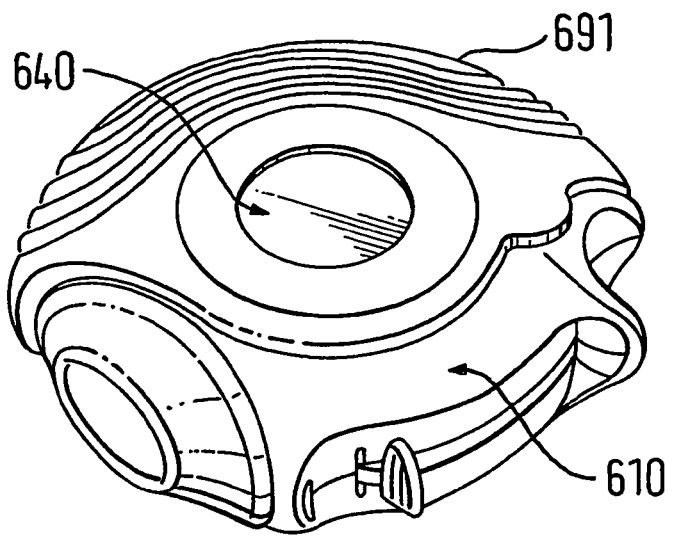
FIGS. 9a and 9b respectively show in assembled and exploded view, a medicament dispenser having an electronic counter with reader in accord with one aspect of the present invention.
Figure 9B:
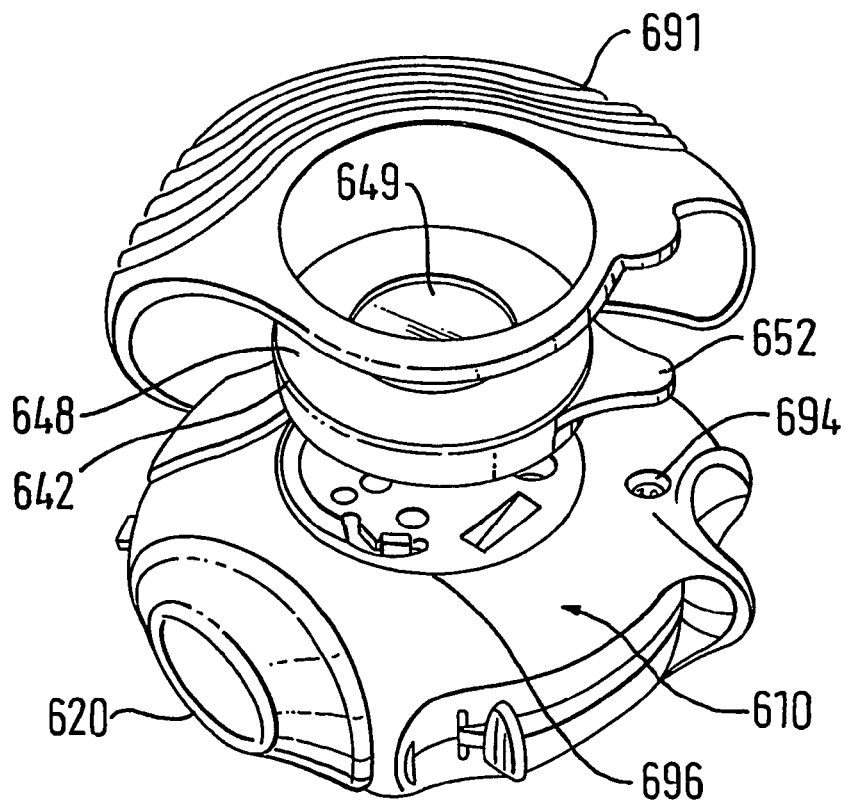

FIGS. 9a and 9b respectively show in assembled and exploded view, a development of the medicament dispenser shown in FIGS. 4 to 7d, in which the dose monitor ring 489 thereof is provided with an electronic reader.

In more detail, the medicament dispenser is provided under a cover 691, which is pivotally mounted to body 610 (as in FIGS. 7a to 7d). The cover 691 is pivotable between an open position (shown in FIG. 8a) in which the mouthpiece 620 is exposed and a closed position in which it is not.

The cover 691 is provided with a circular cut-away portion 696 shaped for receipt of a detachable electronic dose read and display unit 640, which comprises an electronics housing 642 shaped for socket receipt by the cut-away portion 696 of the cover 691; and a protective cover 648 having a display window 649 provided thereto. The housing 642 houses electronic components including a battery; an LCD screen; and a microprocessor chip (not visible). In a preferred aspect, the electronic counter unit 640 is received in snap-fit fashion within the cut-away portion 696 of the cover 691.

The electronic read and display unit 640 is further provided with an electronic reader 652 positioned adjacent to window 694 in the body 610 through which analogue count indicia are visible (e.g. on the dose monitor ring 489, as described in detail in relation to FIGS. 5 and 7a–7d). In use, the reader 652 electronically reads the count displayed through the window 694. That count value is then displayed (in larger size) on the LCD screen of the display unit 640. In effect, the count value is therefore provided to the user in magnified form.

In a variation of the embodiment of FIGS. 9a and 9b, the dose monitor ring 489 of the dispenser of FIGS. 4 to 7d is adapted to display indicia only for the last few (e.g. for the last five) remaining doses or alternatively, to represent those last few indicia in different visual form (e.g. different colour) to alert the user that the number of doses remaining is low.

Figure 10A:
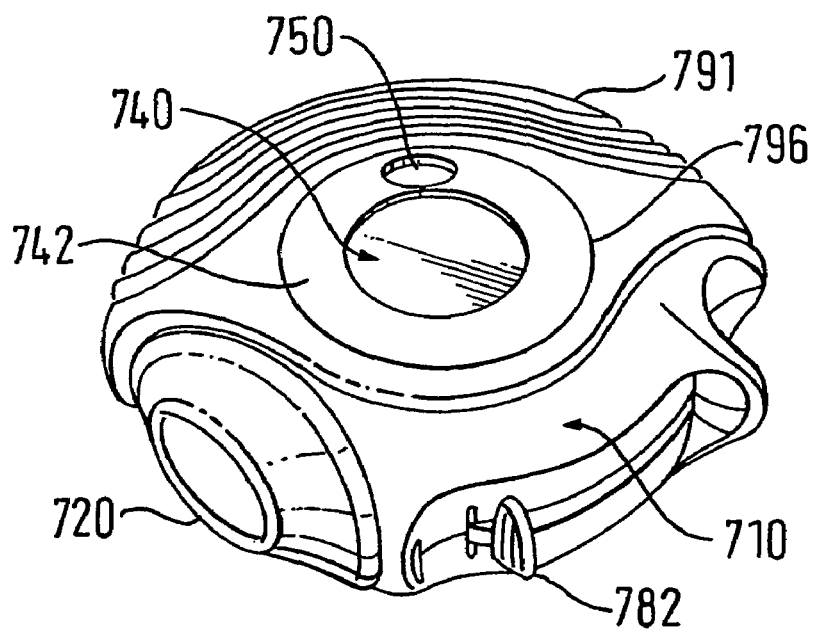
FIG. 10a shows in exploded view, a medicament dispenser having a push-button actuable electronic counter in accord with one aspect of the present invention.

In another embodiment herein, FIG. 10a shows in exploded view, a medicament dispenser having a push-button actuable electronic counter. The dispenser may be seen to be an adaptation of the dispenser of FIGS. 4 to 7d.

In more detail, the dispenser is provided under a cover 791, which is pivotally mounted to body 710. As before, the cover 791 is pivotable between an open position in which the mouthpiece 720 is exposed and a closed position in which it is not.

Figure 10B:
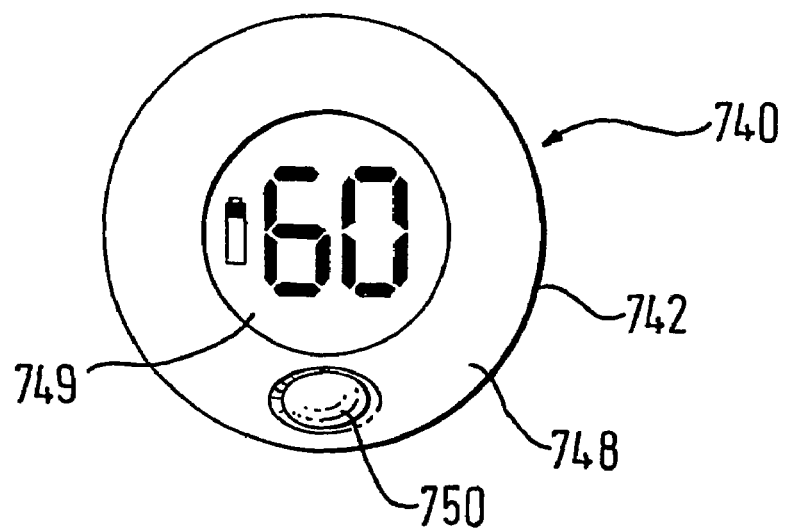
FIG. 10b shows the counter in plan view.

The cover 791 is provided with a circular cut-away portion 796 shaped for receipt of a detachable electronic dose counter unit 740 (shown in FIG. 10b), which comprises an electronics housing 742 shaped for socket receipt by the cut-away portion 796 of the cover 791; and a protective cover 748 having a display 749 provided thereto. The housing 742 houses electronic components including a battery; an LCD screen; and a microprocessor chip (not visible). In a preferred aspect, the electronic counter unit 740 is received in snap-fit fashion within the cut-away portion 796 of the cover 791.

Actuation of the electronic dose counter 740 to register a count is by a user pushing the push-button 750, which sits within the cover 748 of the counter unit 740.

In more detail, in operation, the user moves the cover 791 to its open position and then presses on the finger tab 782 to index the medicament dose (as before). The patient then inhales through the mouthpiece 720 to access the medicament dose, as in the preceding embodiments. The patient also pushes the push button 750 to register that a dose has been accessed and taken.

The electronic counter/display of the embodiments shown in FIGS. 8a to 10b may in aspects, be adapted to display further information of use to the patient. Thus information displayed can for example, include 'dose remaining', 'time since last dose', 'low dose warning', 'dose dispensed from device' and 'replacement dispenser needed'. In addition, visual or audible alarms may also be incorporated.

In further embodiments, medicament dispensers utilising composite features of the variations of the dispensers shown in FIGS. 8a to 10b are envisaged.

Figure 11A:
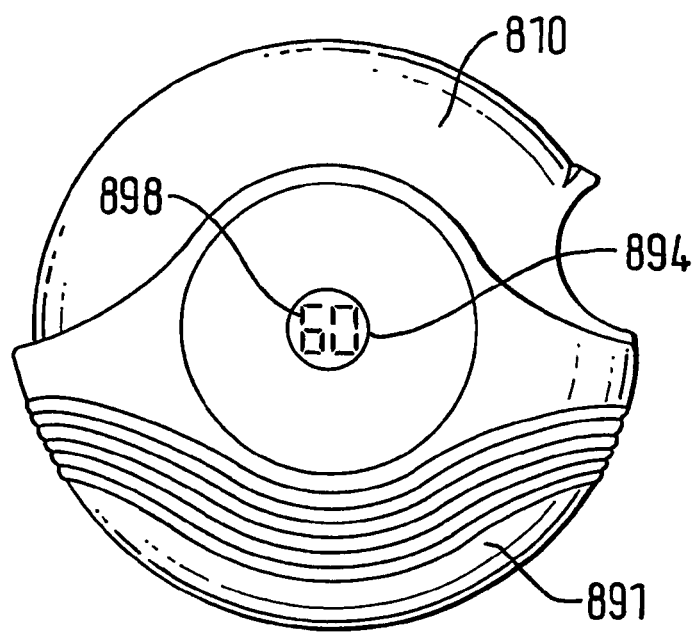
FIGS. 11a and 11b respectively show in plan and cutaway view, a medicament dispenser incorporating a viewer for viewing blister strip having consecutively printed numbers arranged thereon.
Figure 11B:
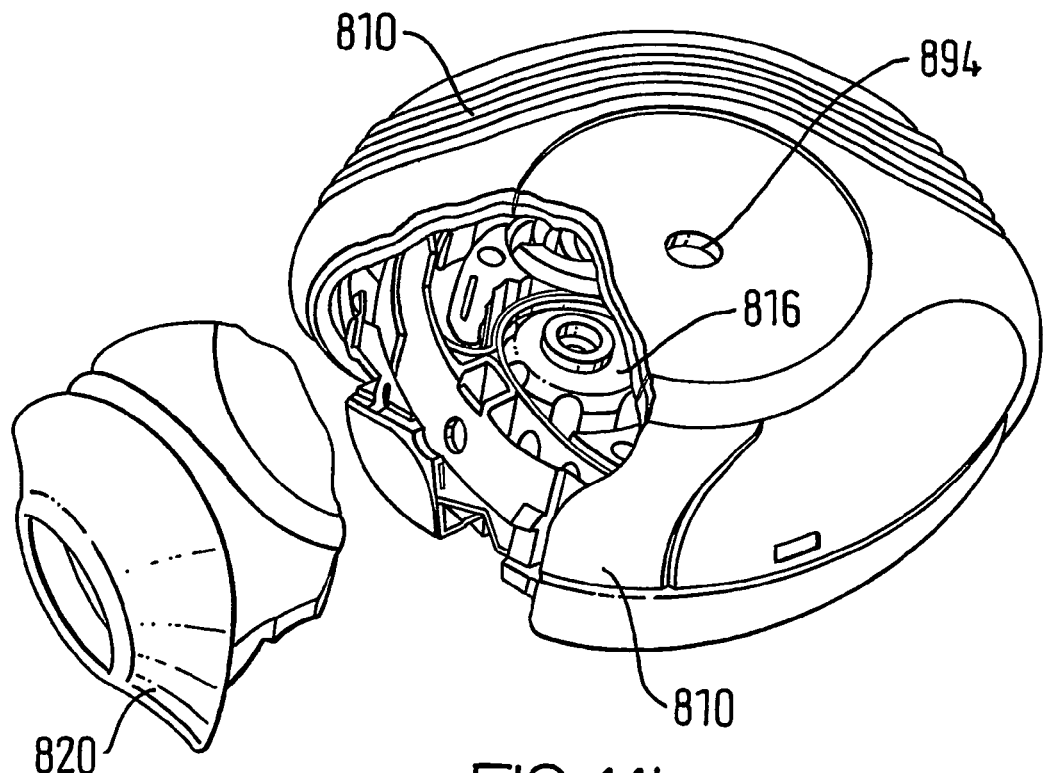

FIGS. 11a and 11b respectively show in plan and cut-away view, a medicament dispenser incorporating a viewer for viewing an elongate blister strip having consecutively printed dose numbers arranged thereon. The dispenser is adapted from the medicament dispenser of FIGS. 4 to 7d.

In more detail, the medicament dispenser is provided under a cover 891, which is pivotally mounted to body 810 (as in FIGS. 7a to 7d). The cover 891 is pivotable between an open position (shown in FIG. 8a) in which the mouthpiece 820 is exposed and a closed position in which it is not. The cover 891 is provided with a viewing window 894 for viewing of dose count indicia 898.

Figure 12:
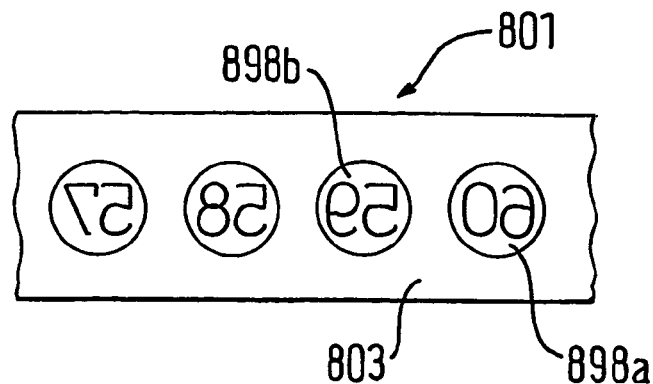
FIG. 12 shows the blister strip in plan view.

The internal mechanism of the dispenser, particularly the mechanism for advancing the blister strip, is essentially as shown in FIGS. 4 to 7d. The elongate blister strip 801 has the form of that shown in FIG. 1, but is adapted as shown in FIG. 12 to have indicia 898a, 898b printed in reverse-character form sequentially on the base sheet 803 thereof. By reverse-character it is meant that the indicia 898a, 898b are presented in reverse (i.e. mirror) image such that when reflected the indicia 898a, 898b display in standard character form. It will be appreciated that the indicia 898a, 898b are spaced along the base sheet 803 such that each indicium 898a is associated with a distinct (i.e. single) medicament dose.

Figure 13A:
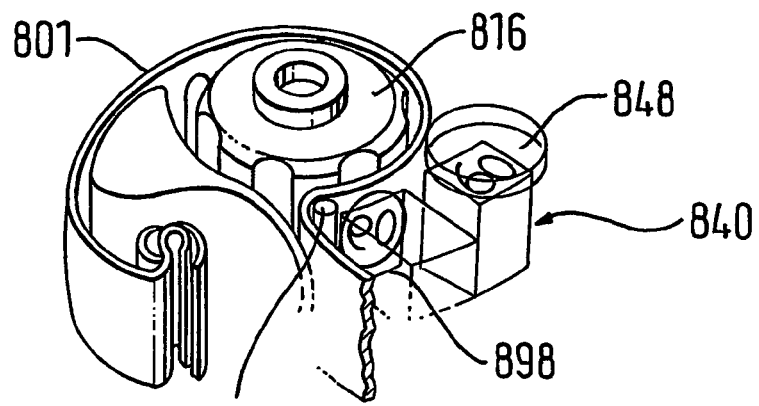
FIGS. 13a and 13b show in plan and side-sectional view, the viewer in more detail.
Figure 13B:
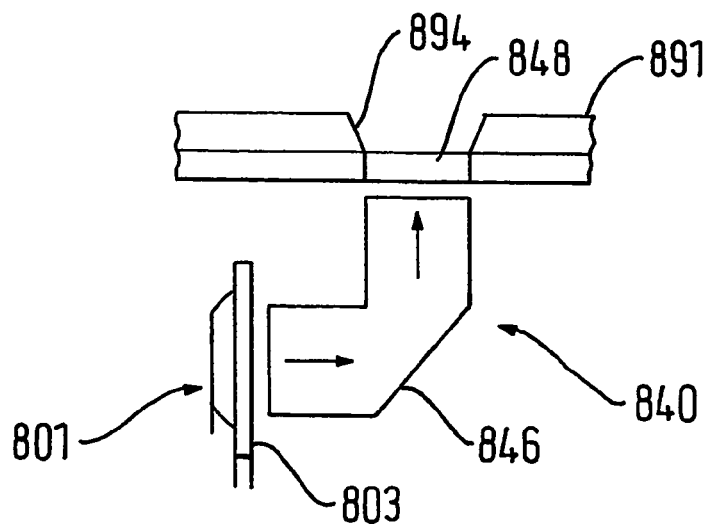

The dispenser is also provided with a prismatic viewer 840 for enabling the viewing of the indicia at the viewing window 894. FIGS. 13a and 13b show the viewer in more detail.

Referring to FIG. 13a, the blister strip 801 is shown adjacent to the index wheel 816 at an opening station 886 (see FIG. 7 for more details of the indexing mechanism). Indicium 898 is visible on the base sheet 803 of the strip 801, whereby the numerical value of that indicium corresponds to the number of the blister pocket received (i.e. opened) at the opening station. Prismatic viewer 840 is located adjacent to the indicium 840 and enables its projection to a viewing position 848, which corresponds to a 90° rotation thereof.

The prismatic viewer 840 is shown in more detail in FIG. 13b, where it can be seen to comprise a 45° angled mirrored surfaced 846 positioned such as to project an image from the base sheet 803 of the strip 801 through 90° to a viewing position 848, which corresponds to the location of the viewing window 894 in the cover 891 of the dispenser.

In use, it will be appreciated that the strip 801 will travel through the dispenser. As this happens, the projected indicia 848 at the viewing window 894 will gradually count down, thereby providing the user with an effective means of determining the number of doses remaining in the dispenser.

It may be appreciated that any of the parts of the dispenser or cassette which contact the medicament suspension may be coated with materials such as fluoropolymer materials (e.g. PTFE or FEP) which reduce the tendency of medicament to adhere thereto. Any movable parts may also have coatings applied thereto which enhance their desired movement characteristics. Frictional coatings may therefore be applied to enhance frictional contact and lubricants (e.g. silicone oil) used to reduce frictional contact as necessary.

The medicament dispenser of the invention is suitable for dispensing medicament combinations, particularly for the treatment of respiratory disorders such as asthma and chronic obstructive pulmonary disease (COPD), bronchitis and chest infections.

Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (e.g. as the sodium salt), ketotifen or nedocromil (e.g. as the sodium salt); antiinfectives e.g., cephalosporins, penicillins, streptomycin, sulphonamides, tetracyclines and pentamidine; antihistamines, e.g., methapyrilene; anti-inflammatories, e.g., beclomethasone (e.g. as the dipropionate ester), fluticasone (e.g. as the propionate ester), flunisolide, budesonide, rofleponide, mometasone e.g. as the furoate ester), ciclesonide, triamcinolone (e.g. as the acetonide) or 6α,9α-difluoro-11β-hydroxy-16α-methyl-3-oxo-17α-propionyloxy-androsta-1,4-diene-17β-carbothioic acid S-(2-oxo-tetrahydro-furan-3-yl) ester; antitussives, e.g., noscapine; bronchodilators, e.g., albuterol (e.g. as free base or sulphate), salmeterol (e.g. as xinafoate), ephedrine, adrenaline, fenoterol (e.g. as hydrobromide), formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol or 4-hydroxy-7-[2-[[2-[[3-(2-phenylethoxy)propyl]sulfonyl]ethyl]amino]ethyl-2(3H)-benzothiazolone; adenosine 2a agonists, e.g. 2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol (e.g. as maleate); α$_4$ integrin inhibitors e.g. (2S)-3-[4-({[4-(aminocarbonyl)-1-piperidinyl]carbonyl}oxy)phenyl]-2-[((2S)-4-methyl-2-{[2-(2-methylphenoxy)acetyl]amino}pentanoyl)amino]propanoic acid (e.g. as free acid or potassium salt), diuretics, e.g., amiloride; anticholinergics, e.g., ipratropium (e.g. as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

Preferred components of the combinations comprise medicaments selected from albuterol, salmeterol, fluticasone propionate and beclomethasone dipropionate and salts or solvates thereof, e.g., the sulphate of albuterol and the xinafoate of salmeterol.

Preferred components of combinations of active ingredients contain salbutamol (e.g., as the free base or the sulphate salt) or salmeterol (e.g., as the xinafoate salt) or formoterol (eg as the fumarate salt) in combination with an anti-inflammatory steroid such as a beclomethasone ester (e.g., the dipropionate) or a fluticasone ester (e.g., the propionate) or budesonide. A particularly preferred combination of components comprises fluticasone propionate and salmeterol, or a salt thereof (particularly the xinafoate salt). A further combination of components of particular interest is budesonide and formoterol (e.g. as the fumarate salt).

Generally, powdered medicament particles suitable for delivery to the bronchial or alveolar region of the lung have an aerodynamic diameter of less than 10 micrometers, preferably less than 6 micrometers. Other sized particles may be used if delivery to other portions of the respiratory tract is desired, such as the nasal cavity, mouth or throat. The medicament may be delivered as pure drug, but more appropriately, it is preferred that medicaments are delivered together with excipients (carriers) which are suitable for inhalation. Suitable excipients include organic excipients such as polysaccharides (i.e. starch, cellulose and the like), lactose, glucose, mannitol, amino acids, and maltodextrins, and inorganic excipients such as calcium carbonate or sodium chloride. Lactose is a preferred excipient.

Particles of the powdered medicament and/or excipient may be produced by conventional techniques, for example by micronisation, milling or sieving. Additionally, medicament and/or excipient powders may be engineered with particular densities, size ranges, or characteristics. Particles may comprise active agents, surfactants, wall forming materials, or other components considered desirable by those of ordinary skill.

The excipient may be included with the medicament via well-known methods, such as by admixing, co-precipitating and the like. Blends of excipients and drugs are typically formulated to allow the precise metering and dispersion of the blend into doses. A standard blend, for example, contains 13000 micrograms lactose mixed with 50 micrograms drug, yielding an excipient to drug ratio of 260:1. Dosage blends with excipient to drug ratios of from 100:1 to 1:1 may be used. At very low ratios of excipient to drug, however, the drug dose reproducibility may become more variable.

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims:

The invention claimed is:

1. A medicament dispenser for use with a medicament carrier having multiple distinct medicament doses carried thereby, said dispenser having an internal mechanism for dispensing the distinct medicament doses carried by said medicament carrier, said mechanism comprising,
   a) receiving means for receiving the medicament carrier;
   b) release means for releasing a distinct medicament dose from the medicament carrier on receipt thereof by said receiving means;
   c) an outlet, positioned to be in communication with the medicament dose releasable by said release means;

d) indexing means for individually indexing the distinct medicament doses of the medicament carrier; and
e) counting means for counting each time a distinct medicament dose of the medicament carrier is indexed by said indexing means, wherein said counting means is provided as a distinct electronic counter unit that is detachable from the medicament dispenser and wherein the electronic counter unit comprises an electronic reader capable of reading an analogue count indicium and an electronic display for displaying said indicium in digital form.

2. A medicament dispenser for use with a medicament carrier having multiple distinct medicament doses carried thereby, said dispenser having an internal mechanism for dispensing the distinct medicament doses carried by said medicament carrier, said mechanism comprising, a) receiving means for receiving the medicament carrier;
b) release means for releasing a distinct medicament dose from the medicament carrier on receipt thereof by said receiving means;
c) an outlet, positioned to be in communication with the medicament dose releasable by said release means;
d) indexing means for individually indexing the distinct medicament doses of the medicament carrier; and
e) counting means for counting each time a distinct medicament dose of the medicament carrier is indexed by said indexing means, wherein said counting means is provided as a distinct electric dose counter unit that is detachable from the medicament dispenser and wherein the electronic counter unit comprises an electronic reader capable of reading an analogue count indicium and an electronic display for displaying said indicium in digital form, wherein the medicament dispenser comprises analogue count means and the analogue count indicium is readable therefrom by said electronic reader.

3. A medicament dispenser for use with a medicament carrier having multiple distinct medicament doses carried thereby, said dispenser having an internal mechanism for dispensing the distinct medicament doses carried by said medicament carrier, said mechanism comprising, a) receiving means for receiving the medicament carrier;
b) release means for releasing a distinct medicament dose from the medicament carrier on receipt thereof by said receiving means;
c) an outlet, positioned to be in communication with the medicament dose releasable by said release means;
d) indexing means for individually indexing the distinct medicament doses of the medicament carrier; and
e) counting means for counting each time a distinct medicament dose of the medicament carrier is indexed by said indexing means, wherein said counting means is provided as a distinct electric dose counter unit that is detachable from the medicament dispenser and wherein the electronic counter unit comprises an electronic reader capable of reading an analogue count indicium and an electronic display for displaying said indicium in digital form, wherein the medicament carrier is provided with analogue count indicia arranged sequentially thereon and readable therefrom by the electronic reader.

4. A medicament dispenser for use with a medicament carrier having multiple distinct medicament doses carried thereby, said dispenser having an internal mechanism for dispensing the distinct medicament doses carried by said medicament carrier, said mechanism comprising, a) receiving means for receiving the medicament carrier;
b) release means for releasing a distinct medicament dose from the medicament carrier on receipt thereof by said receiving means;
c) an outlet, positioned to be in communication with the medicament dose releasable by said release means;
d) indexing means for individually indexing the distinct medicament doses of the medicament carrier; and
e) analogue counting means for counting each time a distinct medicament dose of the medicament carrier is indexed by said indexing means,
f) manipulating means to manipulate an analogue count indicium provided by said analogue counting means, wherein the manipulating means comprises an electronic reader capable of reading an analogue count indicium and an electronic display for displaying a manipulated representation of that indicium in digital form.

5. A medicament dispenser for use with a medicament carrier having multiple distinct medicament doses carried thereby, said dispenser having an internal mechanism for dispensing the distinct medicament doses carried by said medicament carrier, said mechanism comprising, a) receiving means for receiving the medicament carrier;
b) release means for releasing a distinct medicament dose from the medicament carrier on receipt thereof by said receiving means;
c) an outlet, positioned to be in communication with the medicament dose releasable by said release means;
d) indexing means for individually indexing the distinct medicament doses of the medicament carrier; and
e) analogue counting means for counting each time a distinct medicament dose of the medicament carrier is indexed by said indexing means,
f) manipulating means to manipulate an analogue count indicium provided by said analogue counting means, wherein the manipulating means comprises a prismatic viewer capable of acting on the analogue count indicium and causing it to be displayed in manipulated form at a desired viewing position.

* * * * *